(12) United States Patent
Kriesel et al.

(10) Patent No.: US 8,821,454 B2
(45) Date of Patent: Sep. 2, 2014

(54) APPARATUS FOR DISPENSING MEDICINAL FLUIDS AND METHOD OF MAKING SAME

(75) Inventors: Marshall S. Kriesel, St. Paul, MN (US); Richard P. Watts, Morro Bay, CA (US); Donald B. Bivin, Oakland, CA (US); Phillip C. Trenholme, Santa Cruz, CA (US); Joshua W. Kriesel, San Francisco, CA (US); Alan D. Langerud, Plymouth, MN (US)

(73) Assignee: Bioquiddity, Inc., San Francisco, CA (US)

( * ) Notice: Subject to any disclaimer, the term of this patent is extended or adjusted under 35 U.S.C. 154(b) by 1003 days.

(21) Appl. No.: 12/800,356

(22) Filed: May 12, 2010

(65) Prior Publication Data
US 2011/0282300 A1 Nov. 17, 2011

(51) Int. Cl.
*A61M 5/00* (2006.01)
(52) U.S. Cl.
USPC ........................................................ 604/244
(58) Field of Classification Search
USPC ................ 604/244, 132, 131; 422/22; 29/428
See application file for complete search history.

(56) References Cited

U.S. PATENT DOCUMENTS

| | | |
|---|---|---|
| 2,236,084 A | 3/1941 | Brown |
| 2,609,192 A | 9/1952 | Lermont |
| 3,675,597 A | 7/1972 | Oddsen et al. |
| 3,884,228 A | 5/1975 | Hahn |
| 4,146,029 A | 3/1979 | Ellinwood |
| 5,009,251 A | 4/1991 | Pike et al. |
| 5,380,287 A | 1/1995 | Kikuchi et al. |
| 5,395,340 A | 3/1995 | Lee |
| 5,607,418 A | 3/1997 | Arzbaecher |
| 5,632,315 A | 5/1997 | Rose |
| 5,743,879 A | 4/1998 | Kriesel |
| 6,056,716 A | 5/2000 | D'Antonio et al. |
| 6,236,624 B1 | 5/2001 | Kriesel et al. |
| 6,278,221 B1 | 8/2001 | Kasuga et al. |
| 6,355,019 B1 | 3/2002 | Kriesel et al. |
| 6,416,495 B1 | 7/2002 | Kriesel et al. |
| 6,474,394 B2 | 11/2002 | Kuhar |
| 7,828,770 B2 | 11/2010 | Bivin et al. |
| 2002/0114728 A1* | 8/2002 | Kulish et al. ..................... 422/22 |
| 2004/0116847 A1* | 6/2004 | Wall .......................... 604/93.01 |
| 2005/0277882 A1 | 12/2005 | Kriesel |
| 2009/0112163 A1* | 4/2009 | Bivin et al. ................... 604/132 |

* cited by examiner

*Primary Examiner* — Bhisma Mehta
*Assistant Examiner* — Brandy S Lee
(74) *Attorney, Agent, or Firm* — James E. Brunton

(57) ABSTRACT

A dispensing device and the method of making same for dispensing medicaments to a patient that includes a housing, a first assembly connected to the first end of the housing that includes a body portion, and a penetrating sub-assembly. The first assembly also includes a rate control chip of novel construction that is connected to the penetrating sub-assembly and functions to control the rate of flow of medicinal fluid to the patient. Disposed within the housing is a second assembly that includes a shuttle, a collapsible container carried by the shuttle and a plurality of variable force springs that function to thrust the collapsible container into penetrating engagement with the penetrating member of the penetrating assembly and then to collapse the collapsible container to deliver the medicinal fluid to the patient. Connected to the second end of the housing is a novel third assembly that includes an operating member that is threadably connected to the shuttle. The operating member functions to controllably move the shuttle forwardly of the housing. The apparatus also includes a novel locking mechanism that releasably locks the operating member against rotation relative to the shuttle.

8 Claims, 19 Drawing Sheets

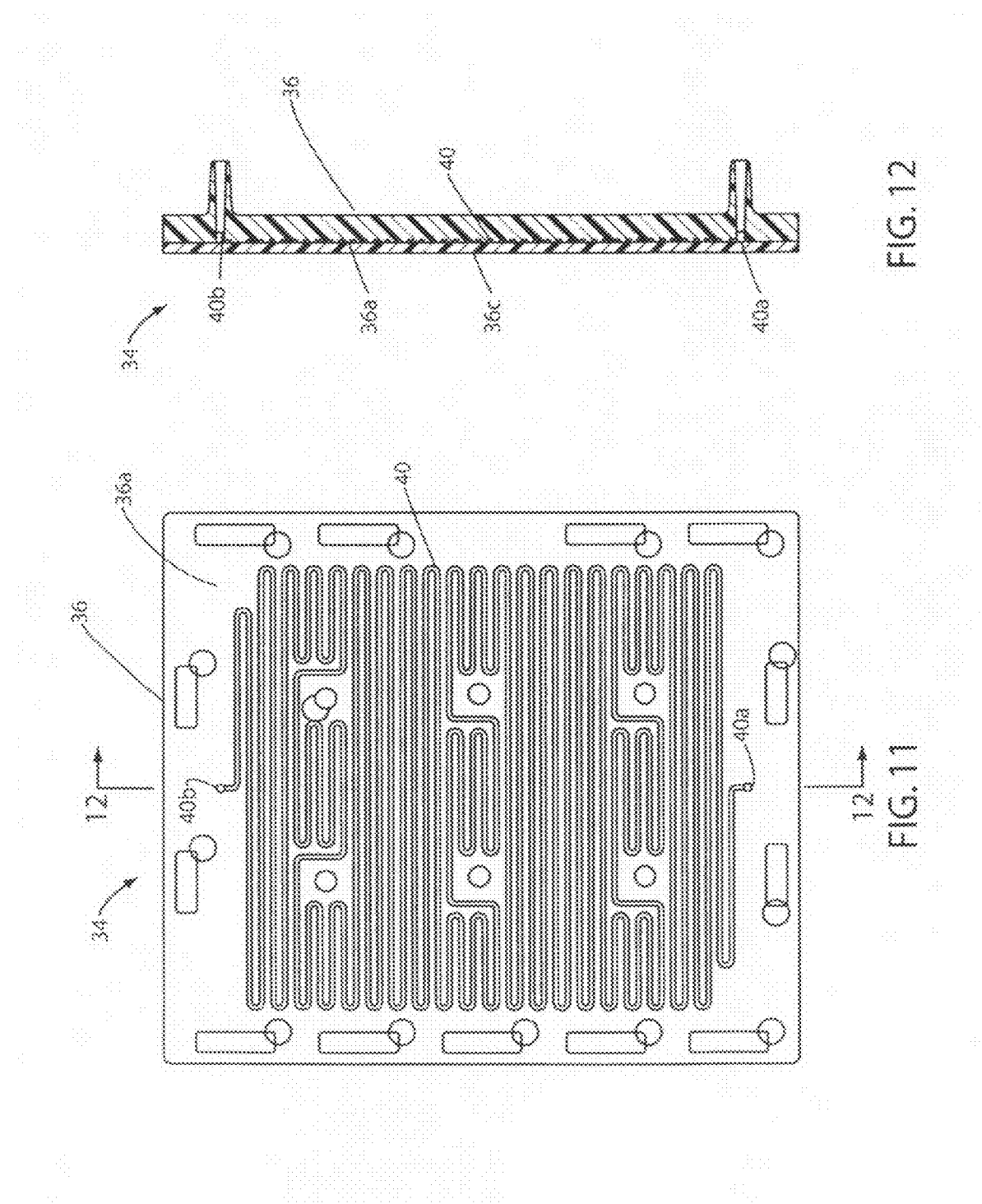

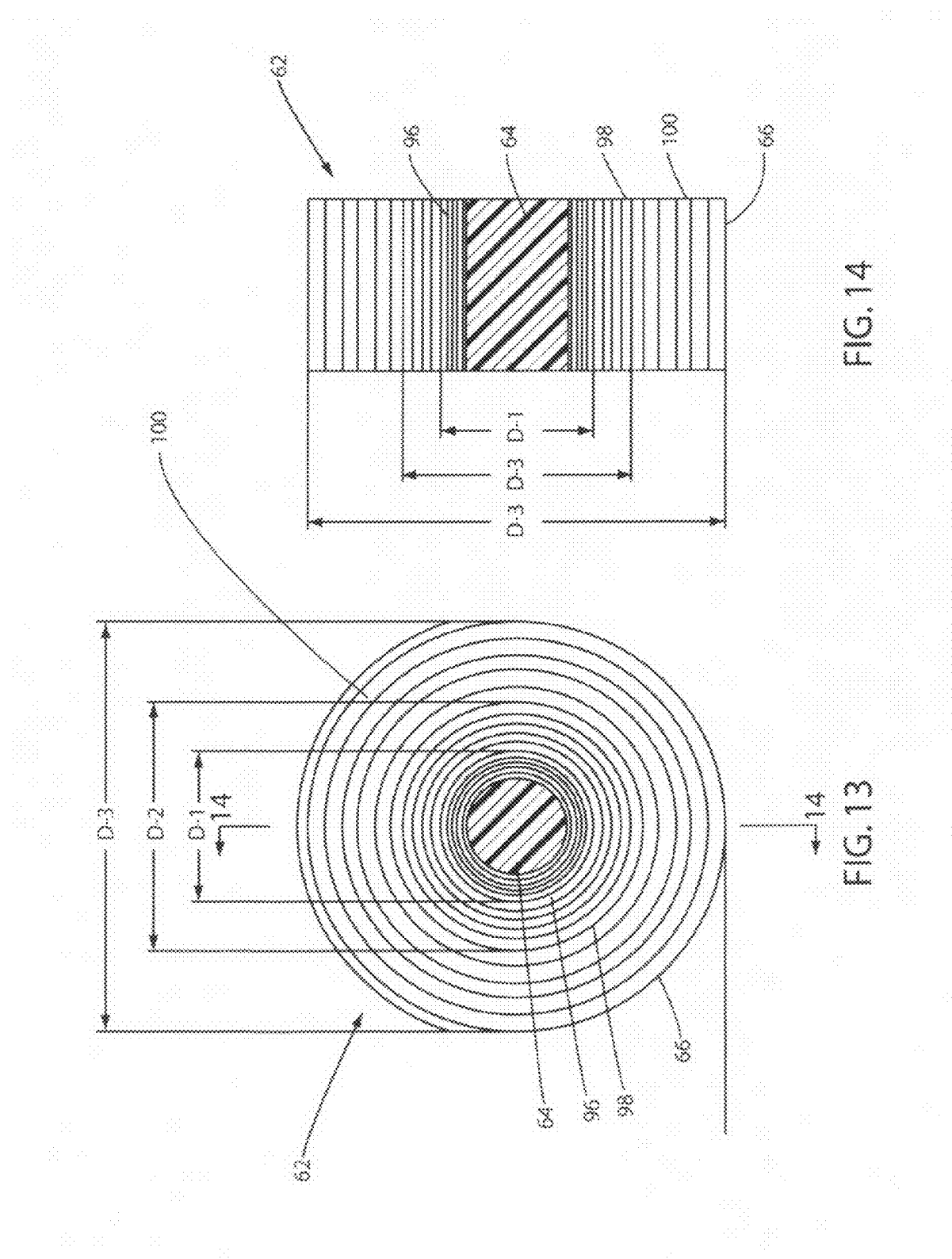

APPARATUS FOR DISPENSING MEDICINAL FLUIDS AND METHOD OF MAKING SAME

CROSS-REFERENCE TO RELATED APPLICATIONS

Not applicable

STATEMENT REGARDING FEDERALLY SPONSORED RESEARCH OR DEVELOPMENT

Not applicable

INCORPORATION-BY-REFERENCE OF MATERIAL SUBMITTED ON A COMPACT DISC

Not applicable

BACKGROUND OF THE INVENTION

1. Field of the Invention

The present invention relates generally to fluid dispensing devices. More particularly, the invention concerns a novel, compact fluid dispenser for dispensing medicinal fluids such as Bupivacaine to ambulatory patients. The fluid dispenser is specifically configured for use at the point-of-care and will allow drug or fluid infusion to be initiated during virtually any phase of care in any healthcare setting, and continue uninterrupted while en-route to other medical facilities or during rehabilitation.

2. Description of Related Art Including Information Disclosed Under 37 CFR 1.97 and 1.98

A number of different types of medicament dispensers for dispensing medicaments to ambulatory patients have been suggested in the past. Many of the devices seek either to improve or to replace the traditional gravity flow and hypodermic syringe methods which have been the standard for delivery of liquid medicaments for many years.

With regard to the prior art, one of the most versatile and unique fluid delivery apparatus developed in recent years is that developed by one of the present inventors and described in U.S. Pat. No. 5,205,820. The components of this novel fluid delivery apparatus generally include: a base assembly, an elastomeric membrane serving as a stored energy means, fluid flow channels for filling and delivery, flow control means, a cover, and an ullage which comprises a part of the base assembly.

Another device for dispensing medicinal fluids to a patient is disclosed in United States Publication No. 2005/0033233 that was published on Feb. 10, 2005. This publication discloses an infusion apparatus with constant force spring energy source for use in controllably dispensing fluid medicaments, such as antibiotics, oncolytics, hormones, steroids, blood clotting agents, analgesics, and bio-pharmaceuticals and like medicinal agents from a reservoir that has been filled from a very short prefilled container. The fluid dispenser includes a housing to which fill vials can be connected for filling the dispenser reservoir with the fluid, and a stored energy source provided in the form of a substantially constant-force spring that provides the force necessary to continuously and uniformly expel fluid from the device reservoir. The fluid dispenser also includes a fluid flow control assembly that precisely controls the flow of the medicament solution to the patient.

Another fluid dispensing device is disclosed in United States Publication No. 2005/0277884 that was published on Dec. 15, 2005. This publication discloses a compact fluid dispenser for use in controllably dispensing fluid medicaments such as antibiotics, analgesics, and like medicinal agents from the device reservoir which is provided in the form of a novel bellows-type assembly. The fluid dispenser includes a unique stored energy mechanism which takes the form of a constant-force spring member of novel design that provides the force necessary to continuously and substantially uniformly expel fluid from the device reservoir. The device also includes novel adjustable flow rate control assembly that is disposed intermediate the fluid reservoir outlet and the outlet port of the device for precisely controlling the rate of fluid flow from the outlet port toward the patient.

Still another fluid dispensing apparatus is disclosed in U.S. Pat. No. 7,220,245. This apparatus comprises a compact fluid dispenser for use in controllably dispensing fluid medicaments such as, antibiotics, oncolylotics, hormones, steroids, blood clotting agents, analgesics, and like medicinal agents from prefilled containers at a uniform rate. The dispenser uniquely includes a stored energy source that is provided in the form of a substantially constant-force, compressible-expandable wave spring that provides the force necessary to continuously and uniformly expel fluid from the device reservoir. The device further includes a fluid flow control assembly that precisely controls the flow of medicament solution to the patient.

BRIEF SUMMARY OF THE INVENTION

By way of brief summary, one form of the apparatus of the invention for dispensing fluids to a patient comprises housing and a first assembly connected to the first end of said housing that includes a body portion and a penetrating sub-assembly that is connected to the body portion. The first assembly also includes a rate control chip of novel construction that is connected to the penetrating sub-assembly and functions to control the rate of flow of medicinal fluid to the patient. Disposed within the housing is a second assembly that includes a shuttle, a collapsible container carried by the shuttle and a plurality of variable force springs that function to thrust the collapsible container into penetrating engagement with the penetrating member of the penetrating assembly and then to collapse the collapsible container to deliver the medicinal fluid to the patient. Connected to the second end of the housing is a novel third assembly that includes an operating member that is threadably connected to the shuttle. The operating member functions to controllably move the shuttle forwardly of the housing. The apparatus also includes a novel locking mechanism that releasably locks the operating member against rotation relative to the shuttle.

With the forgoing in mind, it is an object of the invention to provide an apparatus of the character described that can be used for dispensing medicinal fluids in hospitals, surgery centers, home care, austere environments, and various other alternate sites of care. The fluid delivery apparatus is uniquely configured for use at the point-of-care and will allow drug or fluid infusion to be initiated during virtually any phase of care, in any healthcare setting, and continue uninterrupted, while en-route to other medical facilities or during rehabilitation.

Additionally, the self-contained and therapy-specific nature of the fluid delivery apparatus functions to reduce the probability of costly and potentially life-threatening medication errors.

Another object of the invention is to provide a fluid dispensing apparatus that can be used for controllably dispensing at a uniform rate a wide variety of fluid medicaments, such as Bupivacane, Ropivaciane, Propofol and like medicinals.

Another object of the invention is to provide a fluid dispensing apparatus of the character described in the preceding paragraph in which the first assembly that includes the penetrating sub-assembly and the rate control chip and a portion of the second assembly that includes the collapsible container can be hermetically sealed and sterilized without adversely affecting the medicinal fluid contained within the collapsible container. Another object of the invention is to provide a fluid dispensing apparatus of the aforementioned character that is of simple compact construction and one that can be used by the military in the field and in the home care environment with a minimum amount of training.

Another object of the invention is to allow infusion therapy to be initiated quickly at the point of care without the assistance of a medical professional.

Another object of the invention is to provide a fluid dispensing apparatus of the character described in the preceding paragraphs in which the stored energy source is provided in the form of a variable force spring in which the force variation is achieved by modifying a constant force spring in a manner to controllably vary the cross-sectional mass of the spring along its length.

Another object of the invention is to provide a fluid dispensing apparatus of the character described in the preceding paragraphs in which the stored energy source is provided in the form of a variable force spring in which the force variation is achieved by coiling the band portion of the spring about the spring drum in varying degrees of tightness.

Another object of the invention is to provide a fluid dispensing apparatus of the class described which includes a fluid flow control assembly that precisely controls the flow of the medicament solution to the patient.

Another object of the invention is to provide a fluid dispensing apparatus of the character described in the preceding paragraphs that embodies an integrally formed, aseptically filled, unitary semi-rigid collapsible container that includes a fluid reservoir that contains the beneficial agents to be delivered to the patient.

Another object of the invention is to provide a fluid dispensing apparatus of the class described which is of a lightweight, small diameter construction and one that is reliable in operation.

Another object of the invention is to provide a fluid dispensing apparatus that is easy and inexpensive to manufacture in large quantities.

BRIEF DESCRIPTION OF SEVERAL VIEWS OF THE DRAWINGS

FIG. 11 is a top plan view of one form of the rate control chip assembly of the invention for controlling the rate of fluid flow toward the patient.

FIG. 12 is a cross-sectional view taken along lines 12-12 of FIG. 11.

FIG. 13 is a side elevational of view of one of the variable force springs of the apparatus of the present invention illustrating the method of coiling the band portion of the spring about the spring drum in varying degrees of tightness.

FIG. 14 is a cross-sectional view taken along lines 14-14 of FIG. 13.

DETAILED DESCRIPTION OF THE INVENTION

Definitions

Figure 1:
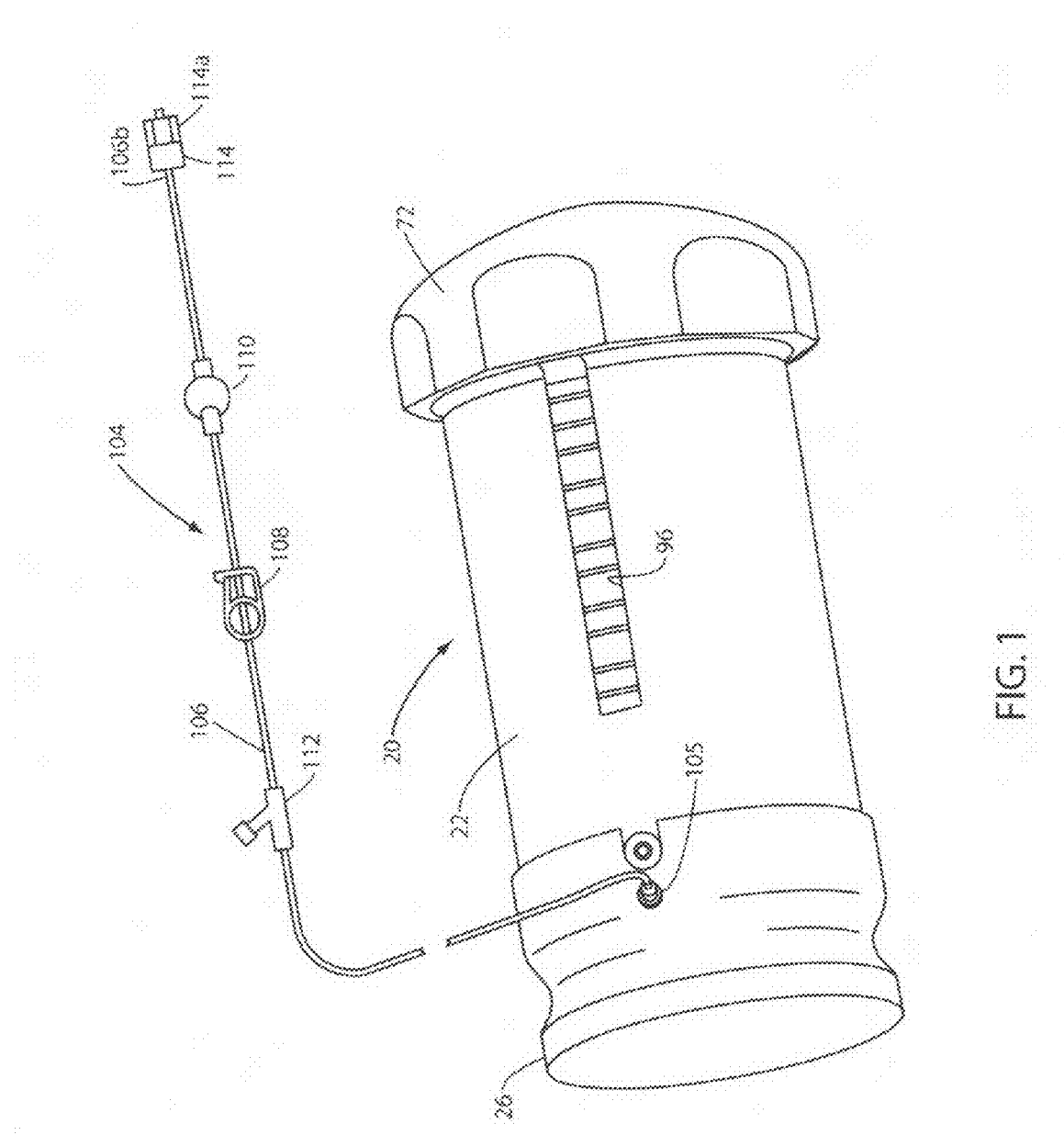
FIG. 1 is a generally perspective view of one form of the apparatus of the invention for dispensing fluids to a patient.

As used herein the following terms mean:
Unitary Container:
A unitary closed container blow molded from a plastic parison.

Continuous/Uninterrupted Wall:

A wall having no break in uniformity or continuity.

Hermetically Sealed Container:

A container that is designed and intended to be secure against the entry of microorganisms and to maintain the safety and quality of its contents after pressurizing.

Aseptic Processing:

The term 'aseptic processing' as it is applied in the pharmaceutical industry refers to the assembly of sterilized components and product in a specialized clean environment.

Sterile Product:

A sterile product is one that is free from all living organisms, whether in a vegetative or spore state.

Blow-Fill-Seal Process:

The concept of aseptic blow-fill-seal (BFS) is that a container is formed, filled, and sealed as a unitary container in a continuous manner without human intervention in a sterile enclosed area inside a machine. The process is multi-stepped; pharmaceutical grade resin is extruded into a tube, which is then formed into a container. A mandrel is inserted into the newly formed container and filled. The container is then sealed, all inside a sterile shrouded chamber. The product is then discharged to a non-sterile area for packaging and distribution.

Collapsible Container:

A dispensing apparatus in which one or more walls of the container are made of a material which will deform (collapse) when pressure is applied thereto; or a dispensing apparatus having a collapsible or telescoping wall structure.

Constant-Force Spring:

Constant-force springs are a special variety of extension spring. They are tightly coiled wound bands of pre-hardened spring steel or stainless steel strip with built-in curvature so that each turn of the strip wraps tightly on its inner neighbor. When the strip is extended (deflected), the inherent stress resists the loading force; the same as a common extension spring but at a nearly constant (zero) rate. The constant-force spring is well suited to long extensions with no load build-up. In use, the spring is usually mounted with the ID tightly wrapped on a drum and the free end attached to the loading force. Considerable flexibility is possible with constant-force springs because the load capacity can be multiplied by using two or more strips in tandem, or back-to-back. Constant-force springs are available in a wide variety of sizes.

Modified Constant-Force Spring (Variable Force Spring):

The modified constant-force spring or variable force spring of the present invention comprises a spring of highly novel configuration that includes an elongated, pre-stressed strip of spring material that may be metal, a polymer, a plastic, or a composite material with built-in curvature so that, like the conventional constant-force spring, each turn of the strip wraps tightly on its inner neighbor. Uniquely, in one form of the invention, the pre-stressed strip of spring material is coiled about the spring drum to predetermined varying degrees of tightness that produces highly specific and desirable linear and non-linear force-distention curves.

Micro-Channel

As used herein, the term of micro-channel means a fluid flow passageway having a width of between about 0.25 in. and about 0.127 in. and a depth of between about 0.25 in. and about 0.127 in.

Ullage

The inwardly extending protuberance formed on the bottom wall of a collapsible container which when the collapsible container is collapsed, substantially fills the upper portion of the container so as to urge substantially all of the fluid from the container.

Figure 2:
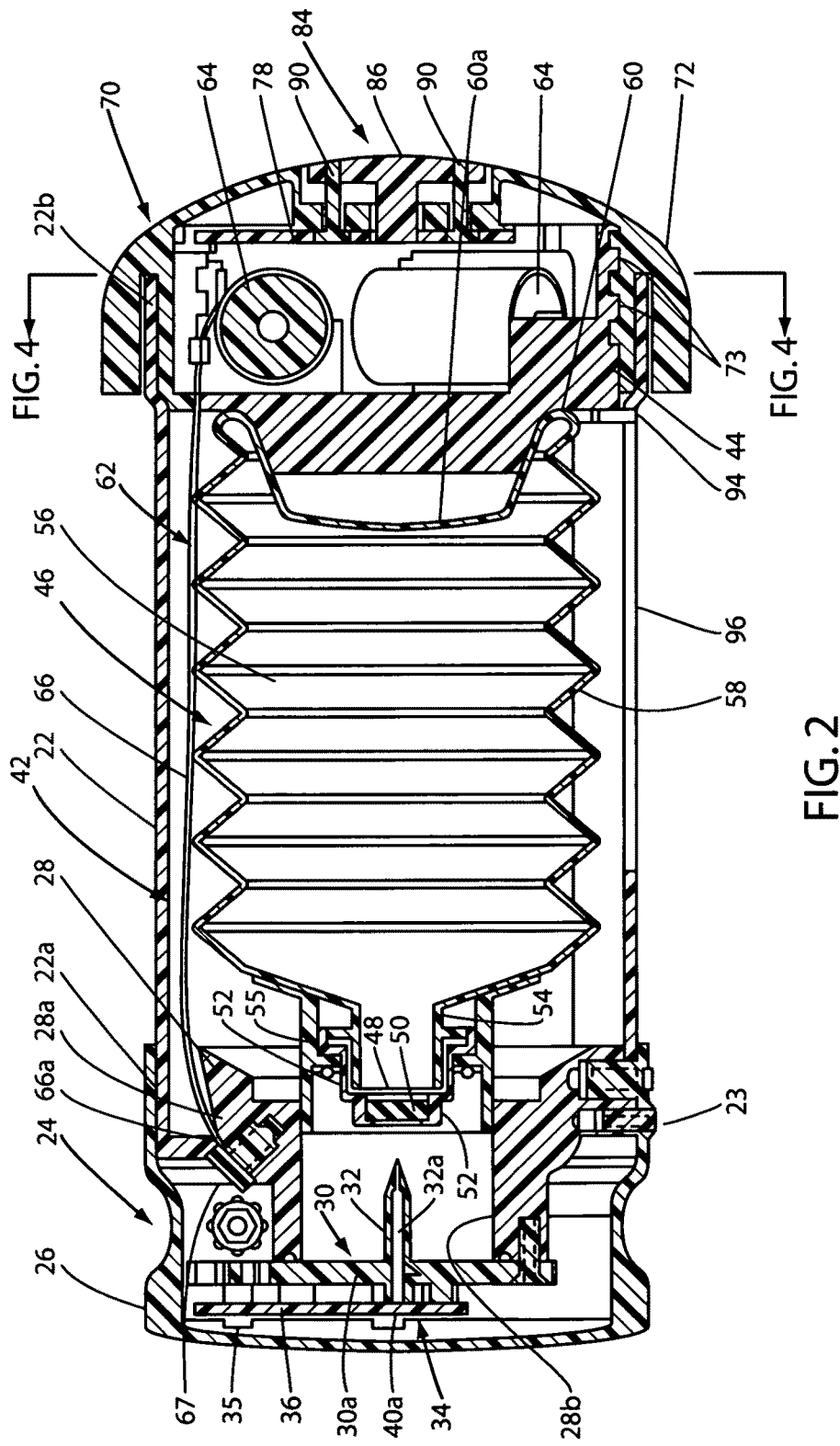
FIG. 2 is a longitudinal cross-sectional view of the housing portion of the apparatus shown in FIG. 1 of the drawings.

Referring now to the drawings and particularly to FIGS. 1 and 2, the operating components of one form of the apparatus of the present invention for dispensing fluids to a patient is there shown. This apparatus, which is generally designated in FIG. 1 by the numeral 20, comprises a housing 22 having first and second ends 22a and 22b. Connected to the first end of housing 22 by conventional connectors 23 is a first assembly 24 that includes a front cover 26. Disposed within front cover 26 are a connector member, or hub 28 and a penetrating sub-assembly 30 that is connected to the connector member. As best seen in FIG. 2 of the drawings, connector member 28 has a shoulder portion 28a and a central bore 28b, the purpose of which will presently be described. Penetrating sub-assembly 30 includes a body portion 30a and a penetrating member 32 that is connected to and extends outwardly from the body portion. Penetrating member 32 has a fluid passageway 32a which, in a manner presently to be described, is in communication with the fluid reservoir of the apparatus.

Also forming a part of first assembly 24 is a novel rate control assembly 34 that is connected to penetrating sub-assembly by conventional connectors 35 in the manner shown in FIG. 2 of the drawings. Rate control assembly 34 includes a rate control member, or chip 36, that is provided with a planar surface 36a having a circuitous micro-channel 40 formed therein. Rate control assembly 34 also includes a very thin, substantially transparent cover 36c that is adhesively bonded to the rate control member (FIG. 12). Micro-channel 40, which for sake of clarity, is viewed in FIG. 11 through the substantially transparent cover 36c, has an inlet 40a that is in communication with the fluid passageway 32a of the penetrating member 32 and an outlet 40b that is in communication with the administration set of the apparatus, the character of which will presently be described. While micro-channel 40 can be of various configurations, it preferably has a width of between about 0.025 in. and about 0.127 in. and a depth of between about 0.025 in. and about 0.127 in.

Figure 3:
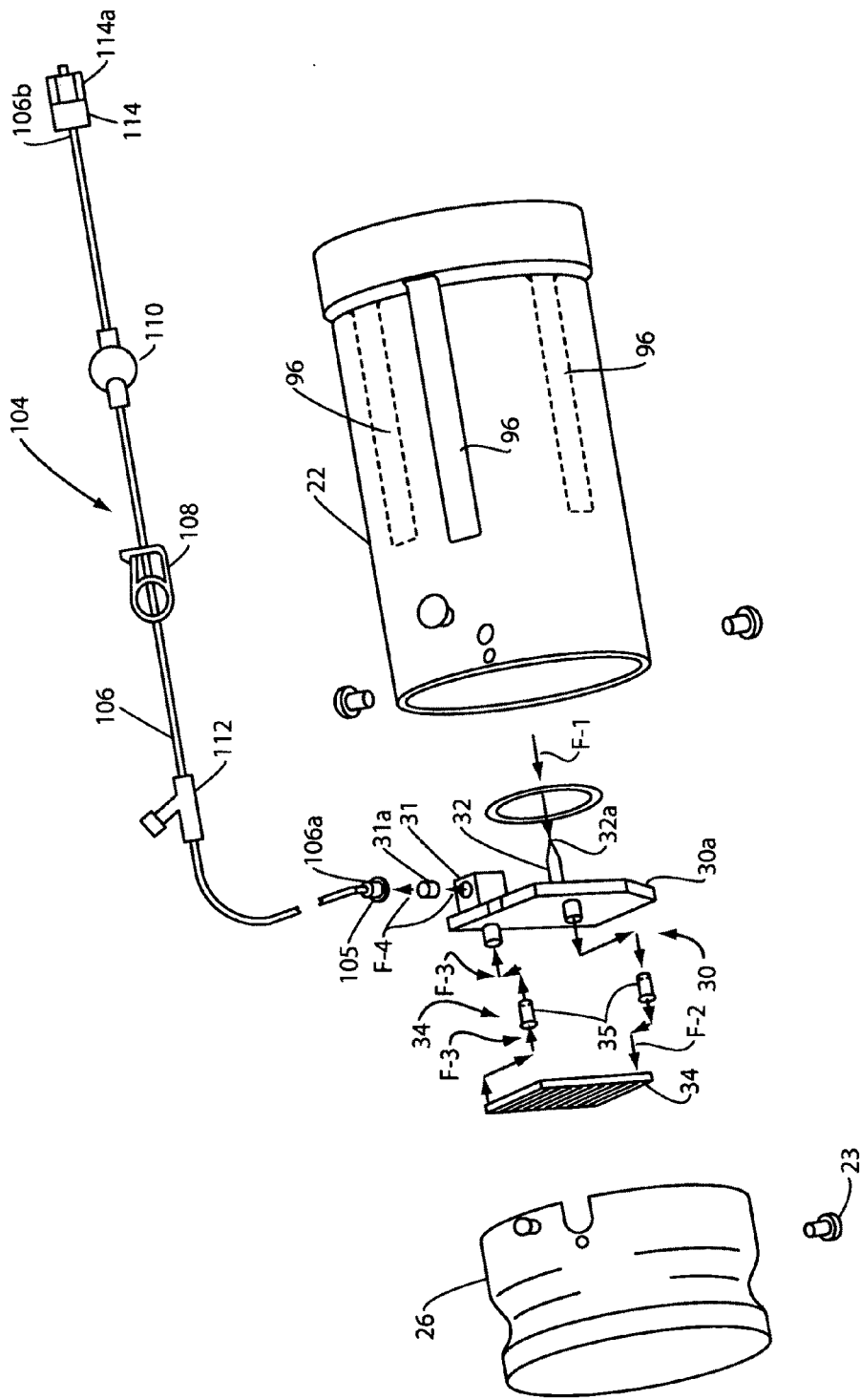
FIG. 3 is a generally perspective exploded view of the forward portion of the apparatus of the invention, including the administration set and illustrating the fluid flow path through the apparatus.
Figure 3A:
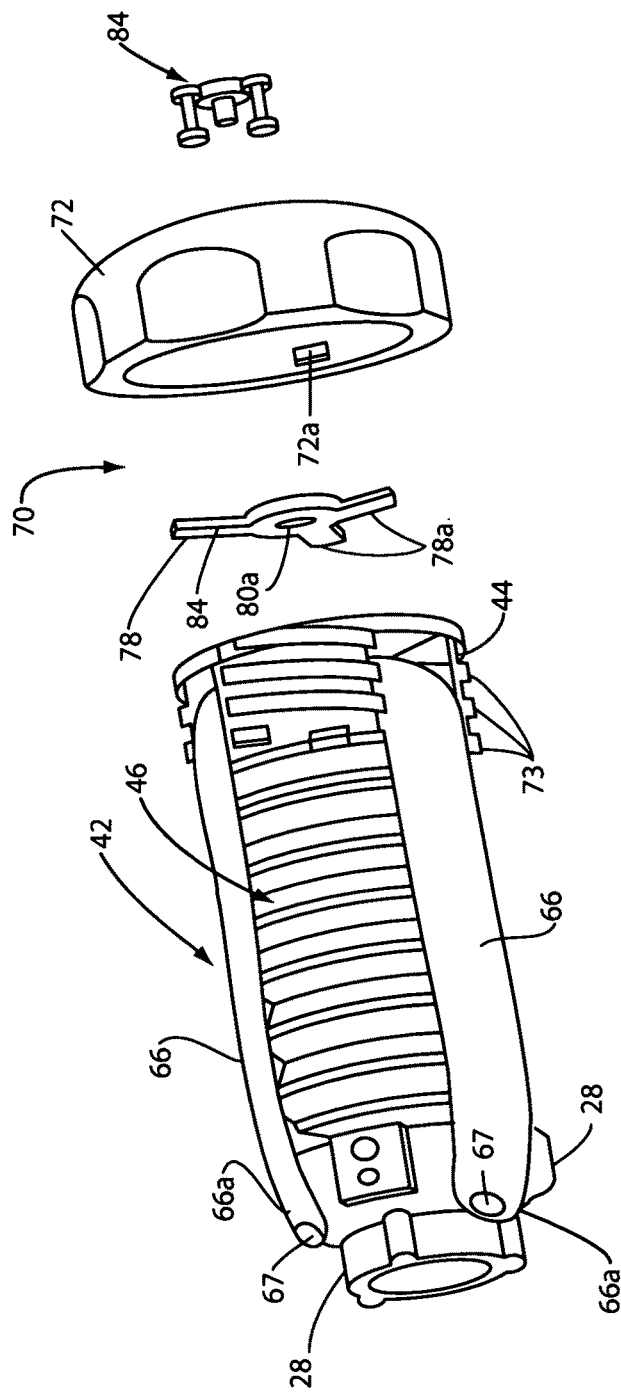
FIG. 3A is a generally perspective exploded view of the rear portion of the apparatus of the invention.
Figure 8:
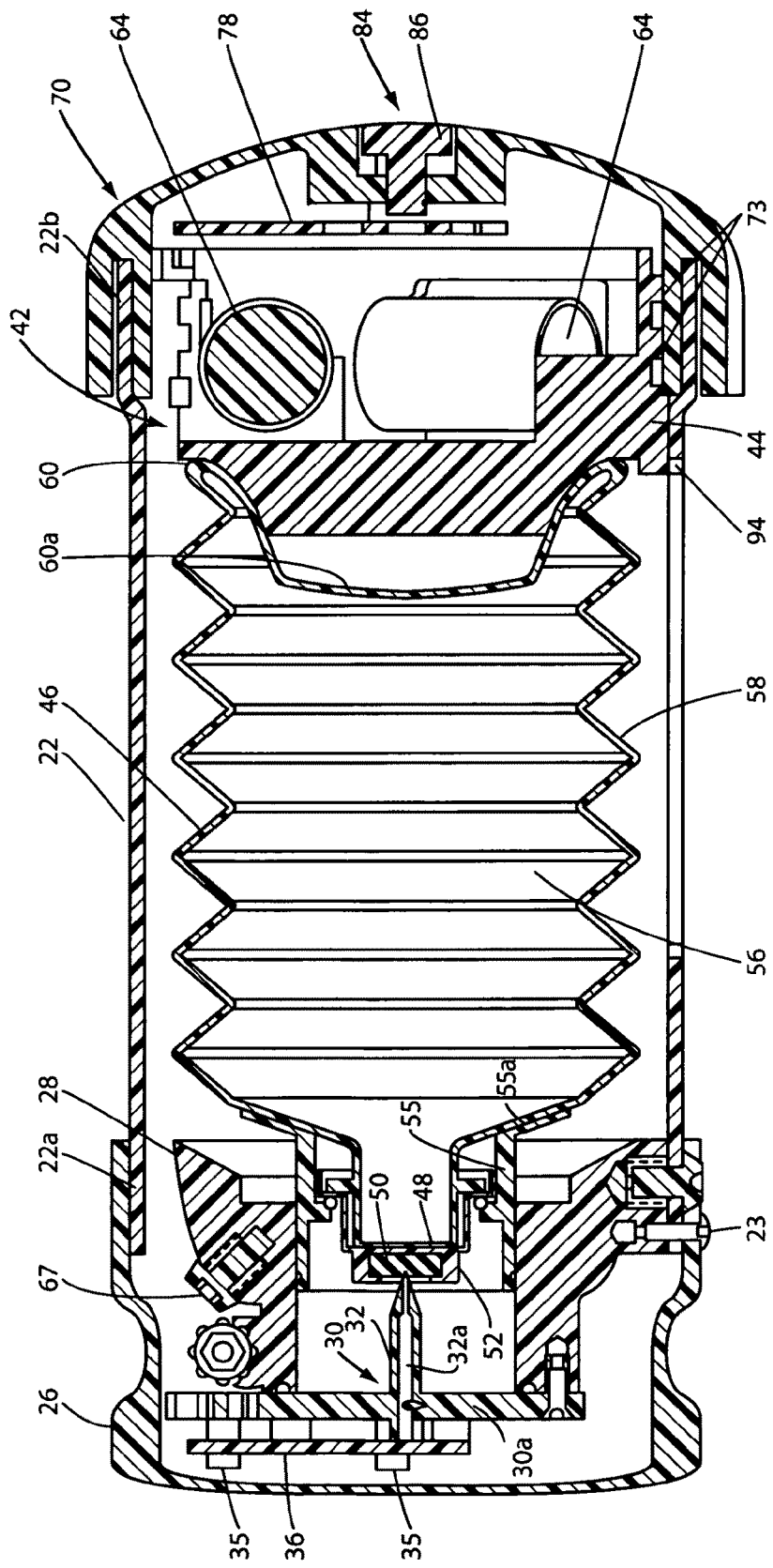
FIG. 8 is a cross-sectional view similar to FIG. 5, but illustrating advancement of the shuttle assembly from the position shown in FIG. 5 as a result of the rotation of the operating assembly relative to the shuttle assembly.

Disposed within the housing 22 is the important second assembly 42 of the invention (see FIG. 3A). A unique feature of the present invention resides in the fact that the second assembly 42 is controllably, progressively movable within housing 32 between a first position shown in FIG. 2 of the drawings, to a second position shown in FIG. 5, to a third position shown in FIG. 8, to a fourth position shown in FIG. 9 and finally, into a fifth position shown in FIG. 10.

In the present form of the invention, the important second assembly 42 comprises a shuttle 44 and a unitary, hermetically sealed collapsible container 46 that is carried by the shuttle in the manner shown in FIG. 2 of the drawings. In the preferred form of the invention, collapsible container 46 is formed in accordance with an aseptic blow-fill-seal manufacturing technique which is of a character well understood by those skilled in the art. This technique involves the continuous plastic extrusion through an extruder head of a length of parison in the form of a hollow tube between and through two co-acting first or main mold halves. The technique further includes the step of cutting off the parison below the extruder head and above the main mold halves to create an opening which allows a blowing and filling nozzle assembly to be moved downwardly into the opening in the parison for molding the molded container. Further details concerning the technique are available from Rommelag GMBH of Stuttgart, Germany and Weiler Engineering of Elgin, Ill.

In a manner presently to be described, collapsible container 46 is accessible via the previously identified penetrating member 32 that is adapted to pierce the closure wall 48 of the collapsible container, as well as a pierceable membrane 50 which is positioned over closure wall 48 by means of a retainer collar 52 which is affixed to the neck portion 54 of the collapsible container 46 and is also affixed to a container positioning collar 55 which circumscribes the neck portion of the container (FIG. 2). Retaining collar 55 also includes a flange portion 55*a* that engages the upper portion of the accordion wall of the container and functions to retain the container in position.

As previously discussed, an important object of the present invention is to provide an apparatus in which the first assembly 24, which includes the penetrating sub-assembly 30 and the rate control assembly 34 and which also includes a portion of the second assembly 42 which comprises the collapsible container 45, can be hermetically sealed and sterilized without adversely affecting the medicinal fluid contained within the collapsible container.

Figure 2A:
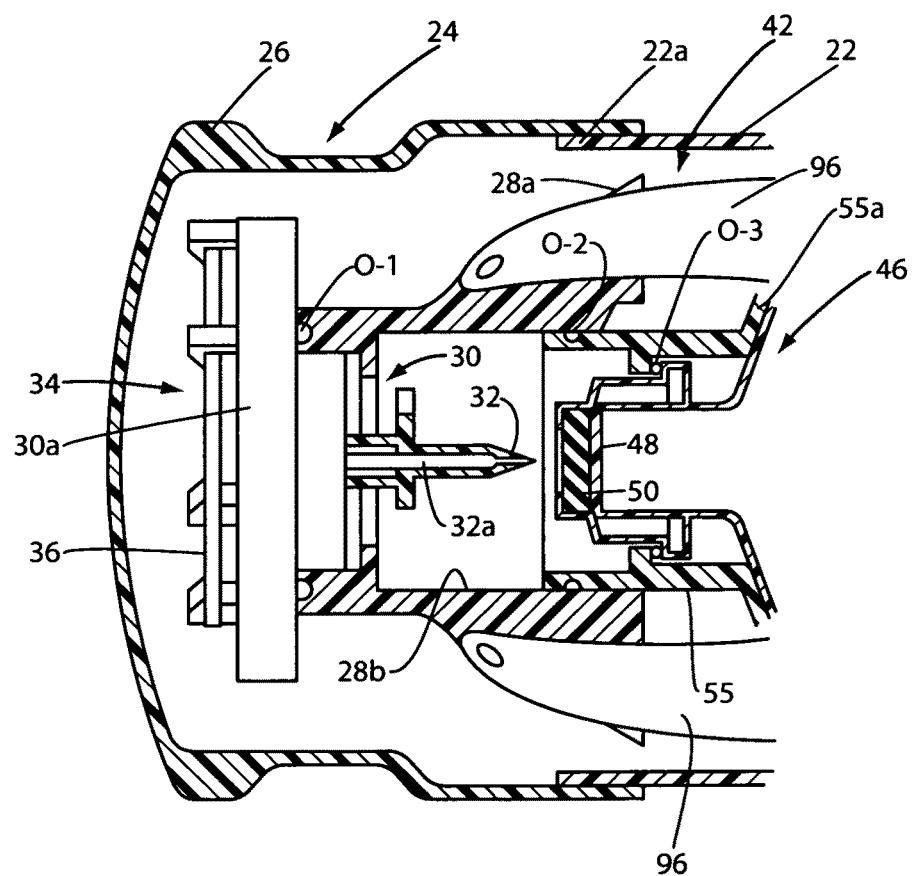
FIG. 2A is a cross-sectional view of the forward portion of the apparatus shown in FIG. 2 of the drawings.

To accomplish this important objective, a plurality of strategically placed O-rings is provided. As best seen in FIG. 2A, a first O-ring O-1 is provided on the upper portion of connector member, or hub 28, and is arranged to sealably engage the body portion 30*a* of penetrating sub-assembly 30. Similarly, a second O-ring O-2, which is provided on the retaining collar 55, is adapted to sealably engage the inner wall portion of the connector member 28. Additionally, a third O-ring O-3, which is carried by the neck portion 54 of the collapsible container 46, is disposed in sealing engagement with a reduced diameter portion 55*a* of the retaining collar 55. With this arrangement, the penetrating sub-assembly 30, the rate control chip 36, and a portion of the second assembly 42 which includes the collapsible container 45, can be effectively hermetically sealed.

Figure 2B:
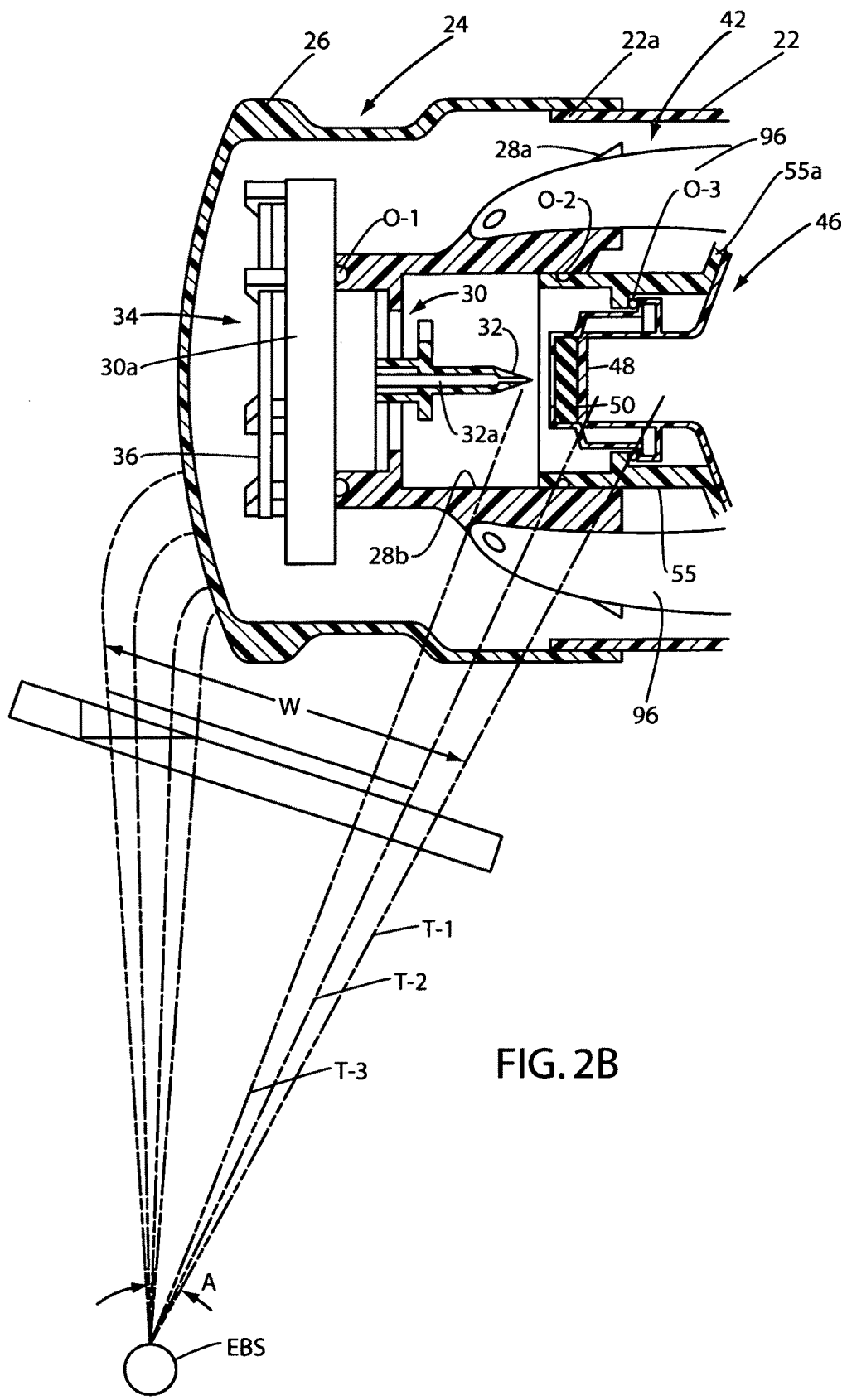
FIG. 2B is a generally diagrammatical view, similar to FIG. 2A illustrating the step of E-Beam sterilization of the forward portion of the apparatus.

Referring next to FIG. 2B of the drawings, the electron beam sterilization step of the present invention is there diagrammatically illustrated. With regard to sterilization, ethylene oxide (EO) and gamma radiation are among the most popular and well established processes for sterilizing polymer-based medical devices. However, these techniques can lead to significant alterations in the materials being treated. Accordingly, sterilization of polymer-based medical devices by electron beam has recently become quite popular and has been proven to be both fast and cost effective.

In accordance with this technique, as electrons scan through polymer-based medical devices, they kill its microbial population by directly breaking microbial DNA chains and by creating secondary particles such as free radicals. These unpaired and highly reactive compounds or atoms further react with the microbes. The damaged DNA keeps microorganisms in the product from reproducing, rendering the product sterile. Further, recent experience has shown that a dose delivered rapidly by electron beam reduces the polymer's degradation and embrittlement. This advantage makes electron beam sterilization a clear choice over gamma sterilization for several polymers which, until now, were perceived as having marginal radiation stability.

As depicted in FIG. 2B and in accordance with the method of the present invention, when the electron beam source EBS is strategically positioned in the manner there illustrated, the critical portions of the apparatus can be effectively sterilized without adversely affecting the medicinal fluid contained within the collapsible container 46. More particularly, by directing the electron beam through a scanning angle of between about 15 and about 20 degrees, through a scanning width of between about 30 and 60 mm and by directing the beam along strategically selected trajectories, such as trajectories T-1, T-2 and T-3, the critical portions of the apparatus such as the penetrating member 32 and the neck 54 of the collapsible container can be effectively sterilized.

Figure 15:
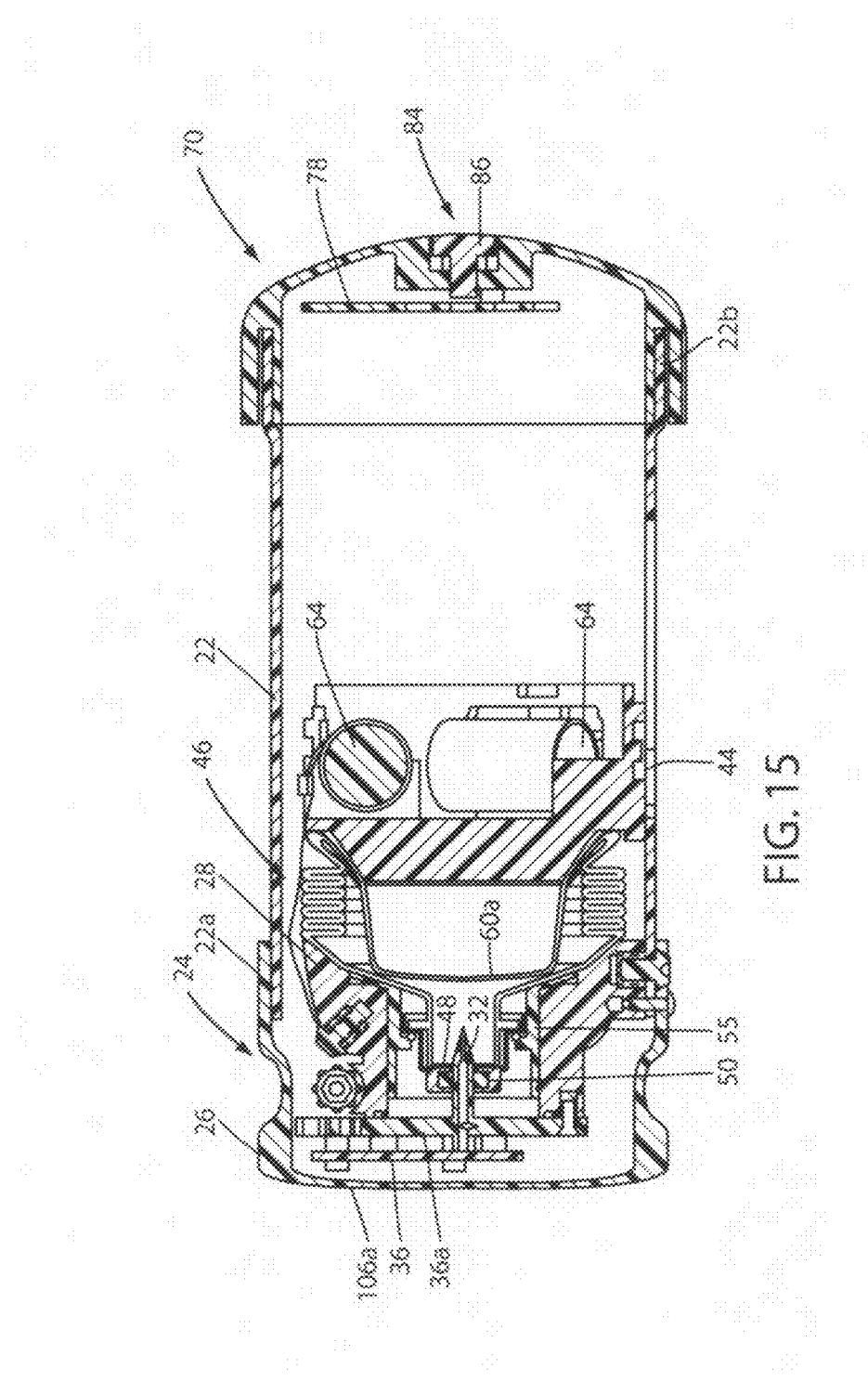
FIG. 15 is a cross-sectional view similar to FIG. 10, but showing the collapsible container of the invention in a collapsed condition following delivery of the medicinal fluid to the patient.

As previously discussed, the basic container 46 of the invention is formed using the earlier described aseptic blow-fill-seal technique and the reservoir portion 56 of the container is sealed by the thin closure wall 48. The pierceable membrane 50 is then positioned over the closure wall and the retainer cap 52 is positioned over the pierceable septal membrane 50 and secured to neck portion 54 by any suitable means such as adhesive bonding, sonic or heat welding. As illustrated in FIG. 2 of the drawings, the collapsible container 46 also includes an accordion shaped sidewall 58 that is integrally formed with said neck portion 54 and a bottom wall 60 that is integrally formed with the accordion shaped sidewall 58. To ensure that the maximum amount of medicinal fluid contained within the collapsible container is dispensed to the patient, bottom wall 60 is provided with an ullage, here provided as an inwardly extending, generally cup-shaped protuberance 60*a*. As illustrated in FIG. 15 of the drawings, when the container is collapsed, protuberance 60*a* resides within and substantially fills the upper portion of the collapsible container that was previously filled with the medicinal fluid. In this way, substantially all of the medicinal fluid contained within the collapsible container is urged therefrom.

Also forming a part of the important second assembly of the invention is a novel stored energy means that is operably associated with shuttle 44 for moving the shuttle 44 and the collapsible container 46 within the housing 22. More particularly, as will be discussed in greater detail hereinafter, the novel stored energy means of the invention uniquely functions to move the shuttle within the housing from the first advanced position shown in FIG. 9 of the drawings to the second advanced position shown in FIG. 10 wherein the piercing member pierces the septal membrane 50 and the pierceable top wall 48 of the collapsible container 46 to open communication between said fluid passageway 32*a* of said penetrating member and the reservoir 56 of said collapsible container. After communication is open between the fluid passageway of the penetrating member and the collapsible container, the stored energy means then moves the shuttle into the third advanced position shown in FIG. 15 wherein the side wall 58 of the collapsible container is collapsed and the medicinal fluid has been delivered to the patient.

Figure 4:
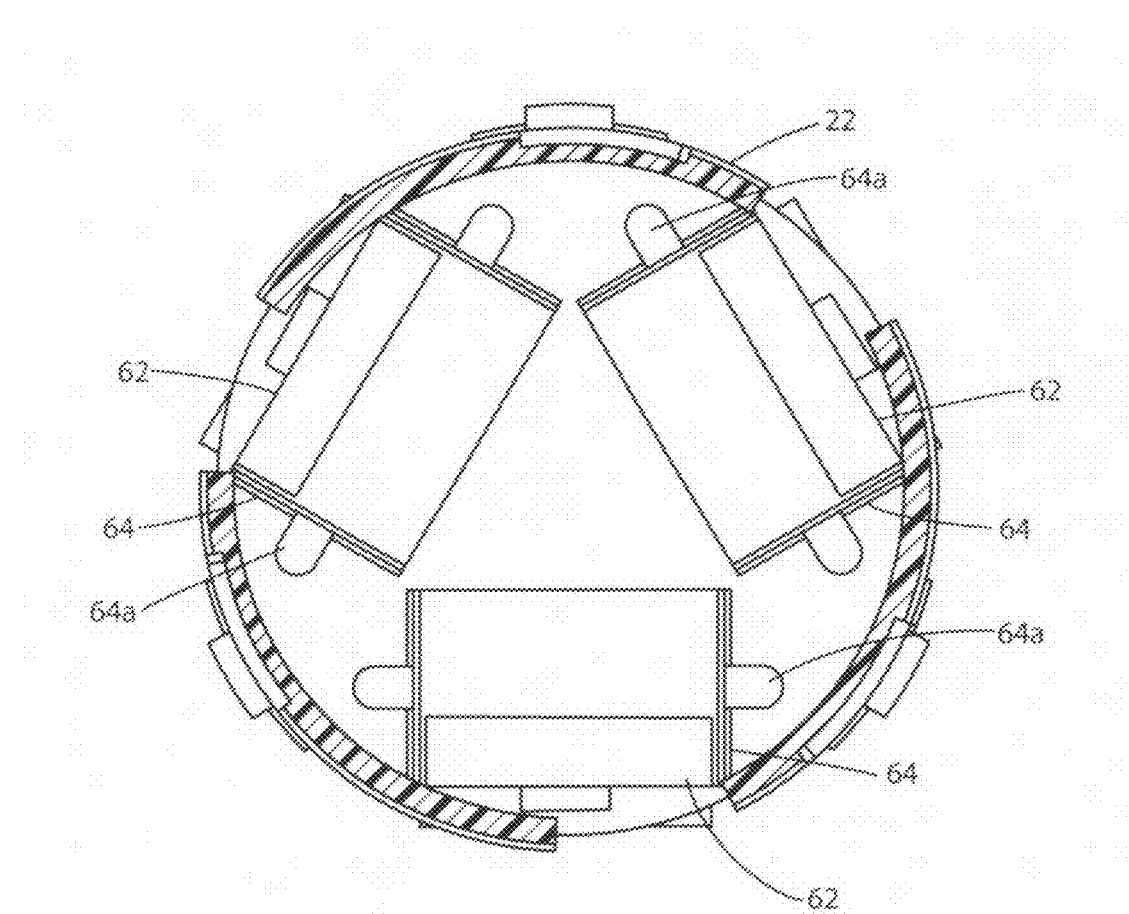
FIG. 4 is a cross-sectional view taken along lines 4-4 of FIG. 2.

In the present form of the invention, this important stored energy means comprises a plurality of circumferentially spaced apart variable force springs 62, each of which comprises a drum assembly 64 and an elongated band of material 66, a portion of which is wound about the drum assembly. Each of the drum assemblies 64, which includes a spindle 64*a*, is carried by the shuttle 44 in the manner illustrated in FIGS. 2 and 4 of the drawings so that the elongate bands 66 extend over the collapsible container and the end portions 66*a* thereof are fixedly connected to the connector member 28 by suitable connectors 67. It is this unique construction that enables the diameter of the housing 22 to be maintained at a minimum.

Variable force springs 62 here comprise constant force springs that have been strategically modified in a manner presently to be described and as illustrated in FIGS. 13 and 14 of the drawings. Conventional constant-force springs of the character that are here strategically modified, which are typically referred to as Negator extension springs, are commercially available from several sources, including Barnes Group Inc. of Bristol, Conn., Stock Drive Products/Sterling Instrument of Hyde Park, N.Y. and Walker Corporation of Ontario, Calif. The conventional constant-force extension spring is basically a high stress, long deflection device that offers great advantages for a variety of applications where very low or zero gradient is desired, where space is a factor and where very high reliability, accuracy, and forced tolerance is required. A constant-force spring is typically a roll of prestressed, strip of metal that exerts a nearly constant restraining force to resist uncoiling. In conventional constant-force springs, the force is constant because the change in the radius of the curvature is constant. The force delivered by a typical prior art constant force spring such as the Negator extension spring, depends on several structural and geometric factors. Structural factors include material composition and heat treatment. Geometric factors include the thickness of the spring, the change in radius of curvature of the spring as the spring is extended, and the width of the spring.

Also forming a part of the apparatus of the present invention is a novel third, or operating assembly 70 that is connected to housing 22 at a location proximate the second end 22b thereof. Third assembly 70 here comprises an internally threaded operating member 72 that is threadably connected to the external threads 73 of the shuttle 44. In a manner presently to be described, controlled manual rotation of the operating member causes the controlled advancement of the second assembly of the invention from the initial position through the second and third, or first advanced position and then into the fourth, or second advanced position.

In the present form of the invention, this important stored energy means comprises a plurality of circumferentially spaced apart variable force springs 62, each of which comprises a drum assembly 64 and an elongated band of material 66, a portion of which is wound about the drum assembly. Each of the drum assemblies 64, which includes a spindle 64a, is carried by the shuttle 44 in the manner illustrated in FIGS. 2 and 4 of the drawings so that the elongate bands 66 extend over the collapsible container and the end portions 66a thereof are fixedly connected to the connector member 28 by suitable connectors 67. It is this unique construction that enables the diameter of the housing 22 to be maintained at a minimum.

Figure 6:
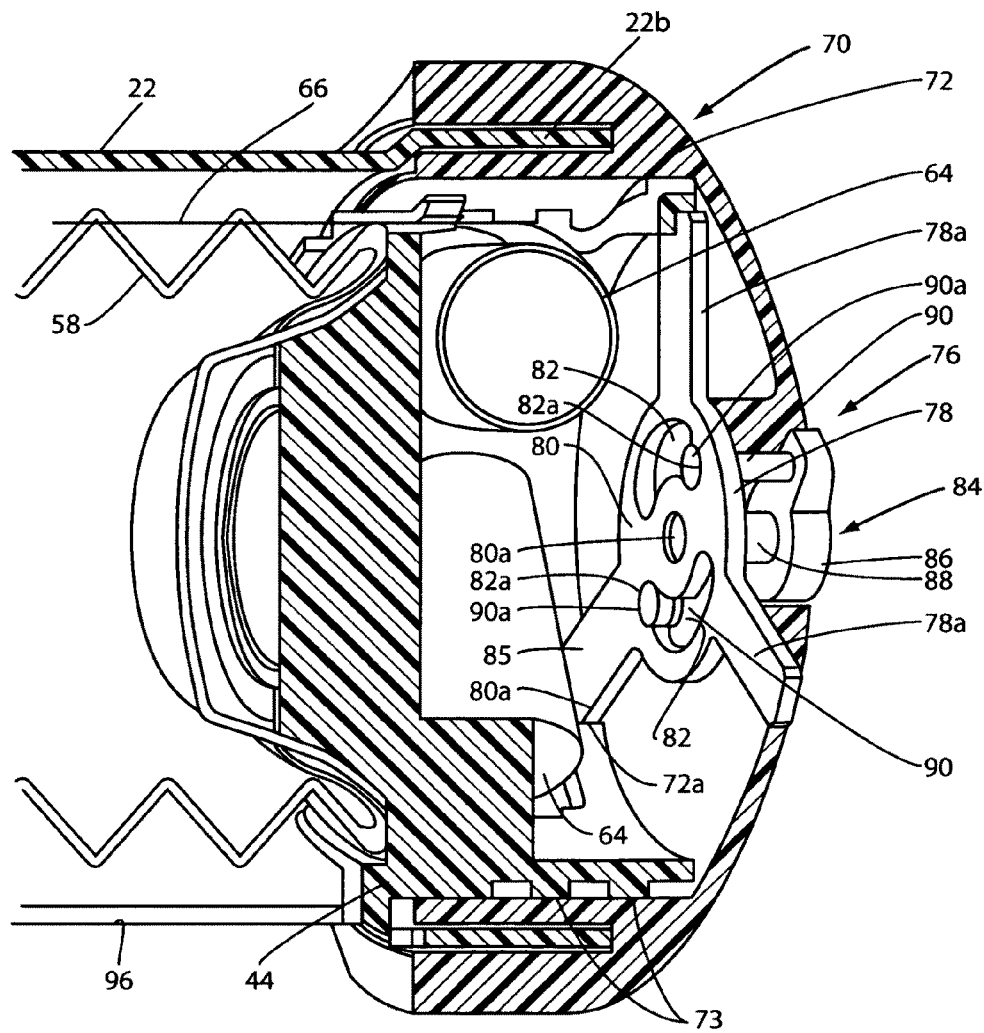
FIG. 6 is a fragmentary, cross-sectional view of the rear portion of the apparatus of the invention showing the locking assembly in a locked configuration to prevent rotation of the operating assembly of the invention.

Third assembly 70 here also comprises a novel manually operated locking assembly 76 that functions to releasably lock the operating member 72 in the first, or starting position shown in FIGS. 2 and 6. Locking assembly 76 here comprises a generally planar locking member 78 that includes a generally circular shaped central portion 80 having a central aperture 80a and a pair of circumferentially spaced, generally arcuate shaped grooves 82 that terminate at one end in semicircular shaped openings 82a. Locking member 78 also includes three circumferentially spaced apart, radially outwardly extending arms 78a.

Figure 5:
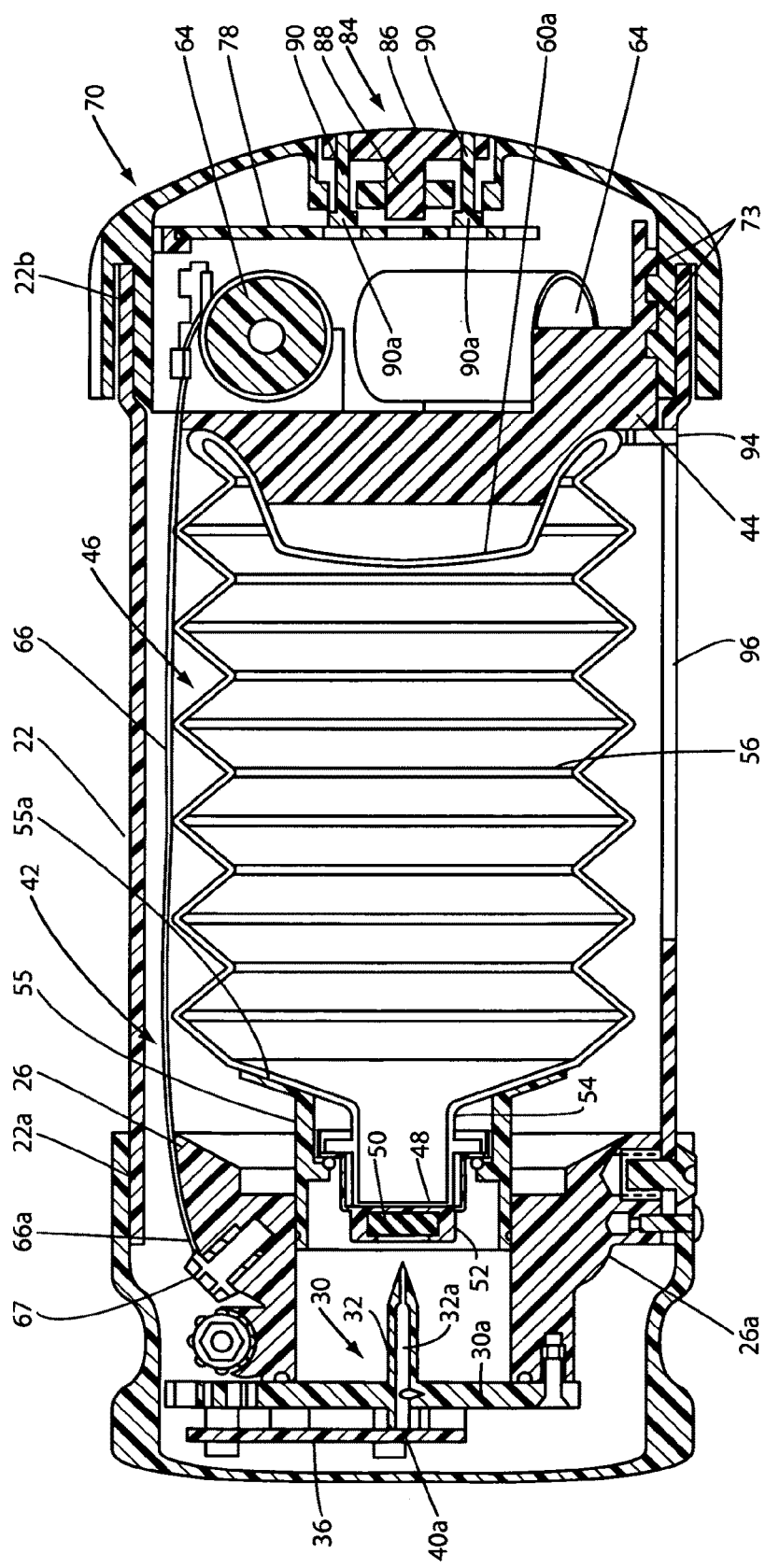
FIG. 5 is a cross-sectional view similar to FIG. 2, but showing the locking assembly in an unlocked configuration to permit rotation of the operating assembly of the invention.
Figure 7:
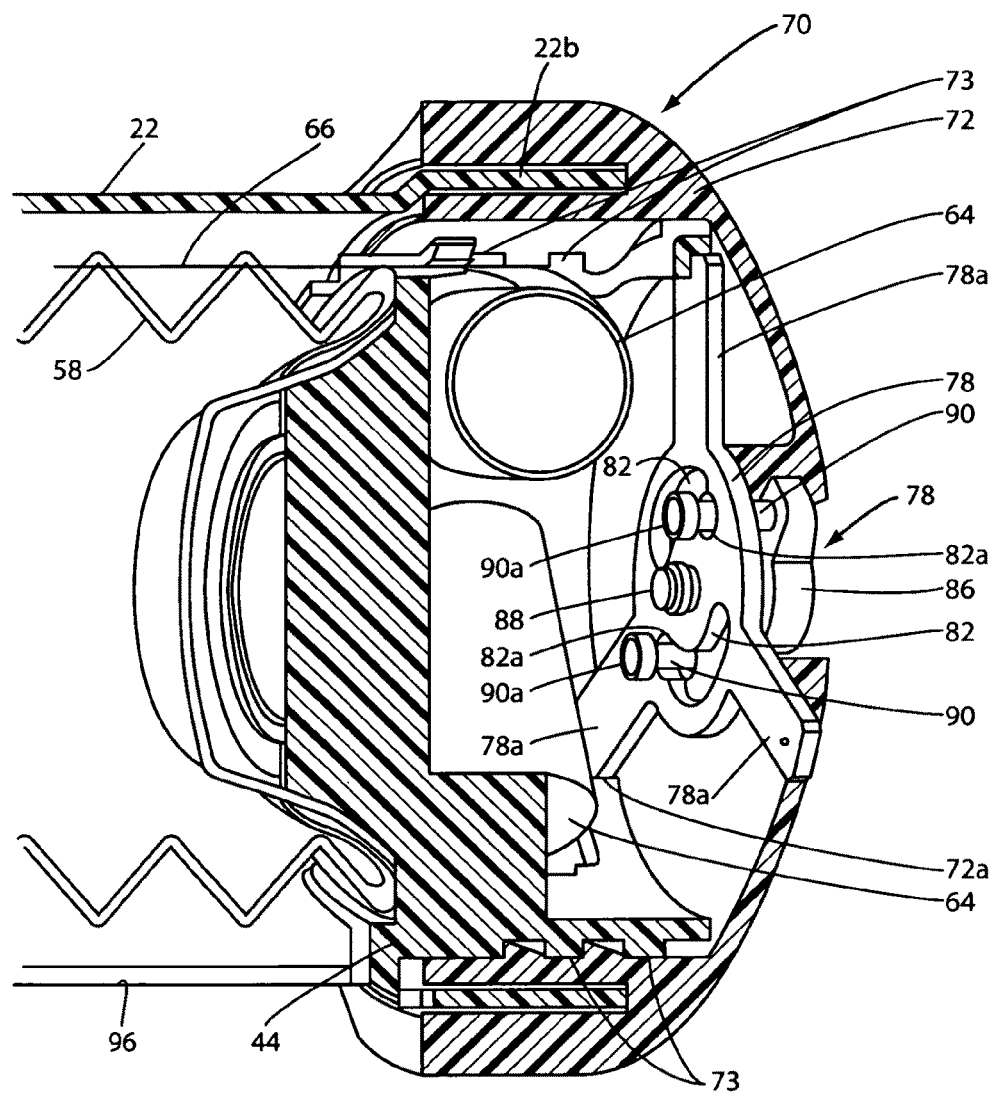
FIG. 7 is a fragmentary, cross-sectional view similar to FIG. 6, but showing the locking assembly in an unlocked configuration to permit rotation of the operating assembly of the invention relative to the shuttle assembly.

Operably associated with the locking member 78 is a pusher assembly that is generally designated in FIGS. 3A and 5 by the numeral 84. This important pusher assembly which is movable between a first extended position shown in FIG. 6 and a second forward position shown in FIG. 7, comprises a pusher member 86 having a centrally located, forwardly extending shaft 88 that is receivable within central aperture 80a of locking member 78. Pusher assembly 84 also includes a pair of forwardly extending shafts 90, each having an enlarged head portion 90a and a cylindrical shaped shaft portion that is receivable within a selected one of the plurality of arcuate shaped grooves 82. When the pusher assembly is in the locked position shown in FIG. 6, the enlarged head portions 90a of the shafts 90 are locked within the semicircular openings 82a, thereby blocking rotation of the operating member 72. More particularly, as best seen in FIG. 6 of the drawings, when the locking assembly is in the retracted position there shown, the extremity of the arm identified in FIG. 6 as 85 is in engagement with a locking shoulder 72a formed internally of the operating member 72. With this construction, any attempt to rotate the operating member will be blocked by the enlarged head portions 90a of the shafts 90. However, when the locking assembly is manually moved into the forward release position shown in FIG. 7, the enlarged head portions of the shafts are moved inwardly relative to locking member 78 and out of engagement with the semicircular openings 82a, thereby permitting rotation of the operating member 72. As the operating member is rotated, the second assembly 42 will be caused to move forwardly of the housing 22 from the position shown in FIG. 2 of the drawings into the position shown in FIG. 5 of the drawings. Continued rotation of the operating member will cause the second assembly to continue to move forwardly of the housing 22 from the position shown in FIG. 2, into the position shown in FIG. 5, and then into the position shown in FIG. 9.

As discussed in the previous paragraph, with the apparatus in the configuration shown in FIGS. 2 and 6, the operating member 72 is locked against rotation relative to the shuttle. Accordingly, in order to commence the fluid delivery process, it is necessary to manually urge the locking assembly inwardly into the release position shown in FIG. 7. Rotation of the operating member will then cause the second assembly 42 to move progressively forward of the housing 22 from the first initial position shown in FIG. 2 of the drawings, to a second position shown in FIG. 5, to a third position shown in FIG. 8 and to a fourth position shown in FIG. 9. As the second assembly moves forwardly of the housing, a plurality of outwardly extending, circumferentially spaced protuberances 94 formed on the shuttle member will slide along within the circumferentially spaced grooves 96 formed in housing 22, thereby guiding its forward movement.

Figure 9:
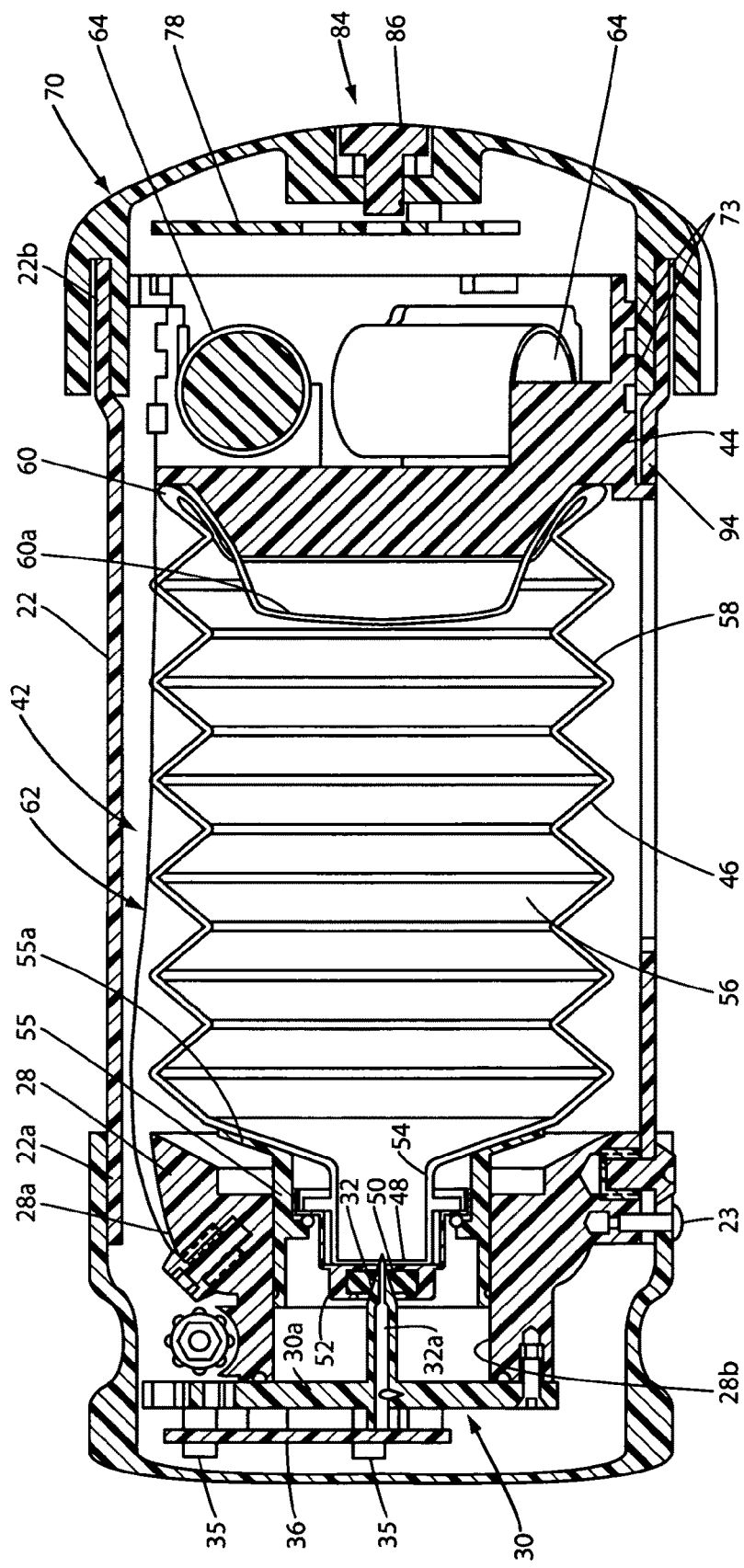
FIG. 9 is a cross-sectional view similar to FIG. 8 illustrating the further advancement of the shuttle assembly from the position shown in FIG. 8 as a result of the continued rotation of the operating assembly relative to the shuttle assembly.
Figure 10:
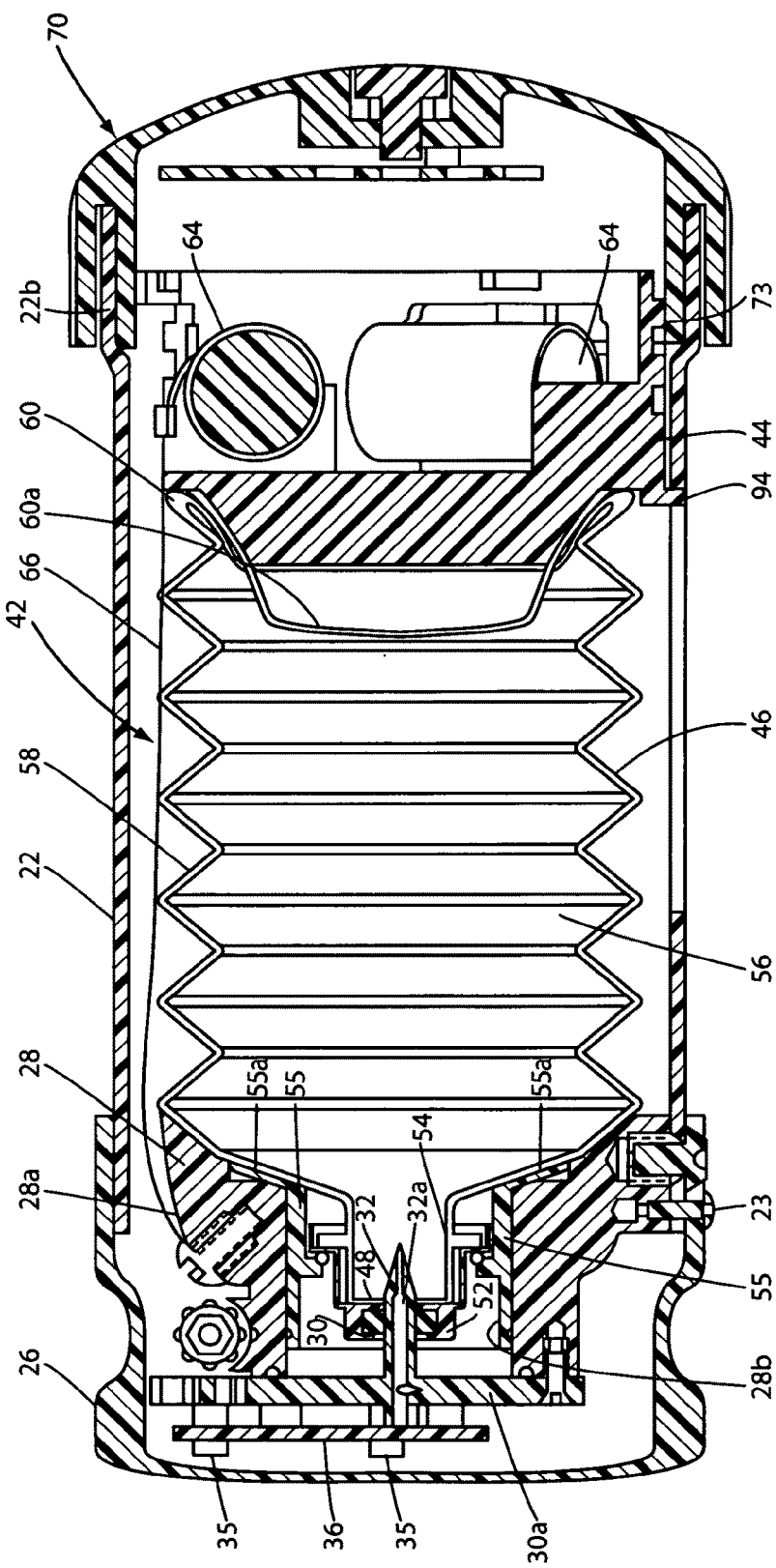
FIG. 10 is a cross-sectional view similar to FIG. 9 illustrating the further advancement of the shuttle assembly from the position shown in FIG. 9 as a result of the variable force springs of the invention acting upon the shuttle assembly.

It is to be noted that when the shuttle 44 reaches the first advanced position shown in FIG. 9 wherein the pierceable top wall of said collapsible container is disposed proximate the piercing member, the threads of the shuttle become free of the threads on the operating member, thereby permitting the variable force springs to wind about their respective drums and in so doing to thrust the collapsible container forwardly of the housing from the first advanced position to a second advanced position wherein the penetrating member 32 will completely pierce the elastomeric septum 50 and the closure wall 48 of the collapsible container in the manner illustrated in FIG. 10 of the drawings.

Once communication is established between the penetrating member 32 and the reservoir 56 of the collapsible container, the variable force springs 62 will continue to wind about their respective drums and in so doing will cause the shuttle to move forwardly into a third advanced position shown in FIG. 15 of the drawings wherein the side wall of said collapsible container is collapsed. As the container collapses, the protuberance 60a will move toward the neck of the container and into the position shown in FIG. 15 wherein it fills a substantial portion of the reservoir of the collapsible container. As illustrated in FIG. 3 of the drawings, as the container collapses, the medicinal fluid contained within the reservoir will controllably flow from the reservoir in the direction of the arrow "F-1" into the internal passageway 32a of the penetrating member 32.

As previously mentioned, the stored energy means of the present invention which functions to collapse the collapsible container 46, here comprises a plurality of circumferentially spaced, variable force springs 62. Each of the variable force springs comprises a drum assembly 64 and a band of material 66 having a first portion wound about the drum assembly and a second end portion 66a connected to the body portion 28 of first assembly 24. Referring to FIGS. 13 and 14 of the drawings, one example of the coiling method of the variable force springs 62 is there illustrated. In accordance with this coiling method, the band portion of the spring is initially wound tightly about the drum 64 to produce a first segment 96 having a diameter "D-1". This done, the band portion is then coiled, or wound more loosely about the drum 64 to produce a second segment 98 having a diameter "D-2". Finally, the band portion is coiled, or wound even more loosely about the drum 64 to produce a third segment 100 having a diameter "D-3".

By coiling the springs about their respective drums with a variation of coil tightness in the manner described in the preceding paragraph and as illustrated in FIGS. 13 and 14, springs having highly specific and desirable linear and non-linear force-distention curves can be produced which will meet the fluid delivery requirements of the invention.

Spring assemblies, such as those depicted in FIGS. 13 and 14 of the drawings, that exhibit a variation of coil tightness that produce highly specific and desirable linear and non-linear force-distention curves to meet the fluid delivery requirements of the invention, are available by custom order from various sources, including Vulcan Mfg. & Spring Company of Telford, Pa.

As previously discussed, with the construction described in the preceding paragraphs, as the accordion-like side wall 58 of the container 46 collapses in a controlled manner in the manner illustrated in FIG. 15 of the drawings, fluid will flow from reservoir 56 into the flow passageway 32a of penetrating member 32 (see FIG. 3). From the penetrating member, the fluid will flow in the direction of the arrow "F-2" into the inlet 40a of the micro-channel 40 of the rate control means of the invention which functions to precisely control the rate of fluid flow from the fluid reservoir 56 toward the patient. After flowing through the micro-channel 40 at a controlled rate, the fluid will flow in the direction of the arrows "F-3" into the connector block 31 (FIG. 3) and then in the direction of the arrows "F-4" into the proximal end 106a of line 106 of the administration set 104 via conventional connectors 31a and 105. It is apparent that by varying the geometry, including the length, width and depth of the micro-channel 40, the rate of fluid flow to the administration set and to the patient can be readily varied.

Disposed between the proximal end 106a and the distal end 106b of the administration line is a conventional clamp 108, a conventional gas vent and a conventional filter 110 and an injector site 112, shown here as a conventional "Y" site. Provided at the distal end 106b of the administration line is a luer connector 114 and luer cap 114a of conventional construction.

As in the earlier described embodiment of the invention, critical portions of the device can be hermetically sealed and sterilized without adversely affecting the medicinal fluid contained within the collapsible container.

Figure 16:
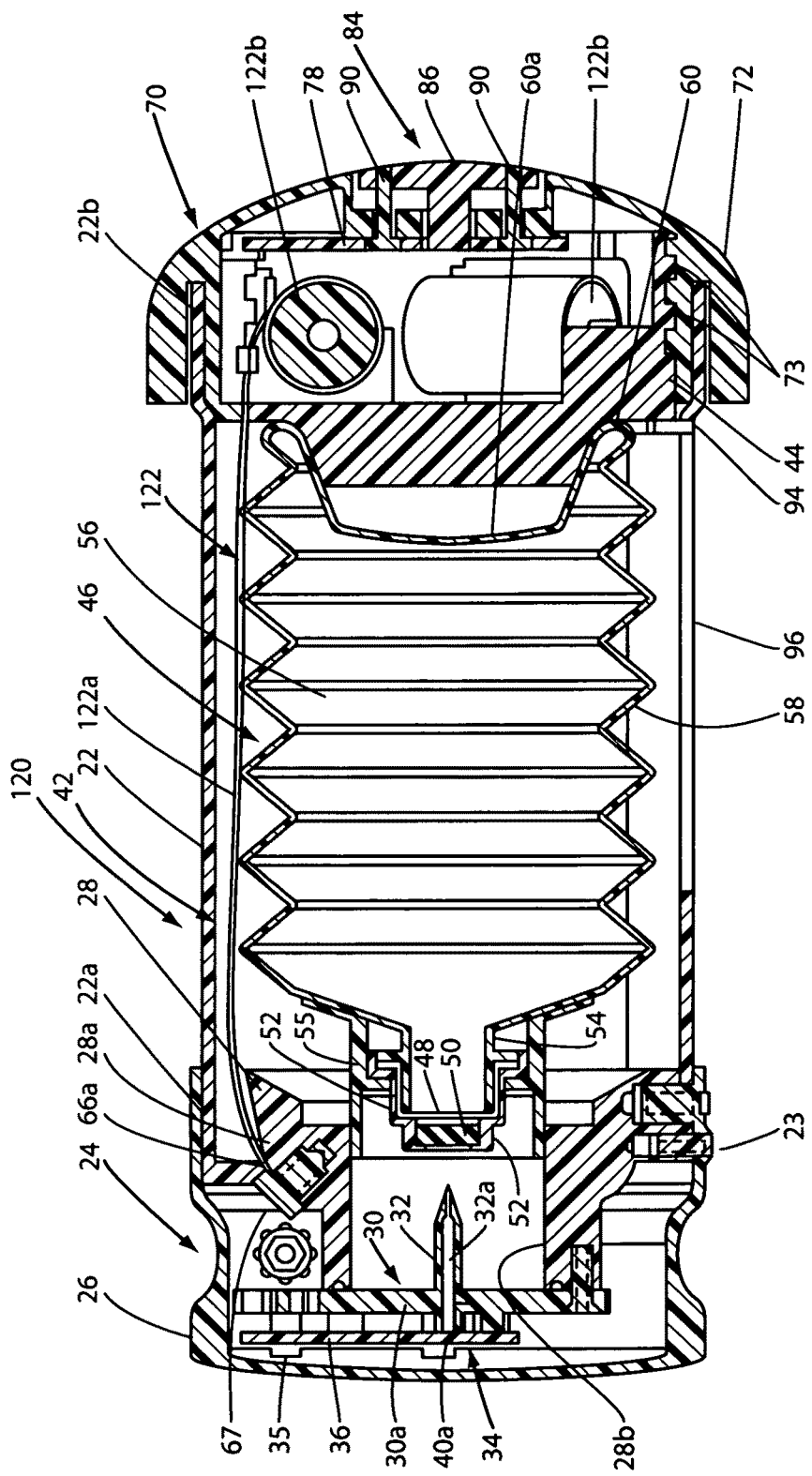
FIG. 16 is a cross-sectional view illustrating an alternate form of the apparatus of the invention for dispensing fluids to a patient.

Referring next to FIG. 16 of the drawings, an alternate form of the apparatus of the invention for dispensing fluids to a patient is there shown. While the second assembly of the apparatus is somewhat different from that of the earlier described second assembly 42 of the earlier described embodiment, the balance of the apparatus is substantially identical in construction and operation to that previously described. Accordingly, like numerals are used in FIG. 16 to identify like components.

As in the earlier described embodiment and as illustrated in FIG. 16 of the drawings, the somewhat differently configured second assembly 120 of this latest form of the invention is disposed within a housing 22 of the character previously described and cooperates with the first and third assemblies 24 and 70 in the manner previously described. During the operation of the apparatus that includes the alternate form of the second assembly 120, the second assembly is progressively movable within housing 22 between a first position, to a second position, to a third position, to a fourth position and, finally, into a fifth position.

Figure 16A:
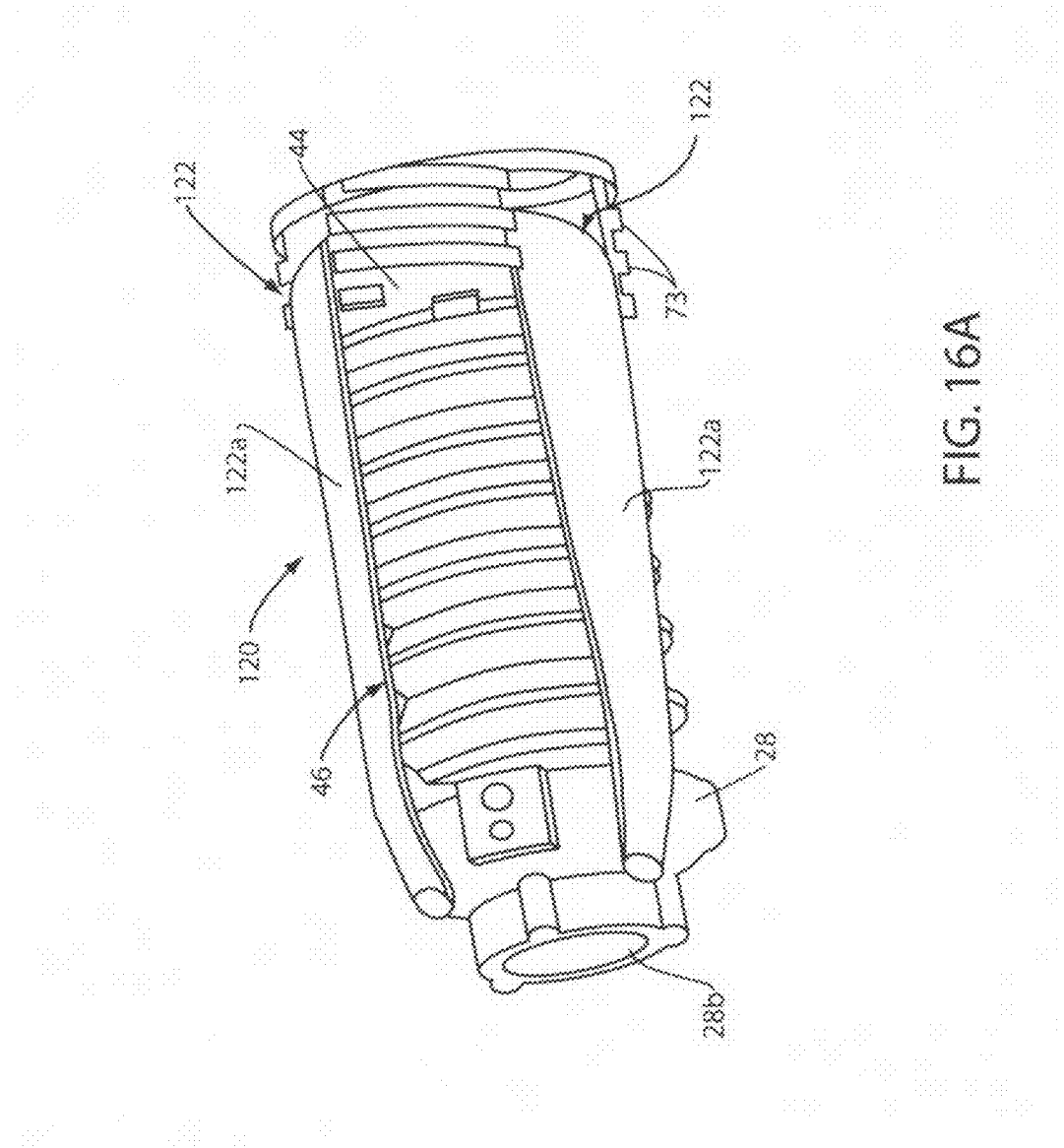
FIG. 16A is an enlarged cross-sectional view illustrating the second assembly of the alternate form of the invention that includes the collapsible container and the stored energy source, shown here as a plurality of tapered springs.

Referring particularly to FIG. 16A of the drawings, it can be seen that second assembly 120 here comprises a shuttle 44 and a unitary, hermetically sealed collapsible container 46 that is carried by the shuttle. In the manner previously described, collapsible container 46 is accessible via the previously identified penetrating member 32 that is adapted to pierce the closure wall 48 of the collapsible container (see FIG. 16), as well as a pierceable membrane 50 which is positioned over closure wall 48 by means of a retainer collar 52 which is affixed to the neck portion 54 of the collapsible container 46 and is also affixed to a container positioning collar 55 which circumscribes the neck portion of the container.

As in the earlier described embodiment of the invention, critical portions of the device can be hermetically sealed and sterilized without adversely affecting the medicinal fluid contained within the collapsible container.

Importantly, this latest form of the invention includes differently configured variable force springs 122. More particularly, the variable force characteristics of the springs of this latest form of the invention are uniquely achieved by varying the cross-sectional mass of the elongated band portion of the spring. Here, the variable cross-sectional mass of the spring is achieved by a constant force spring that has been modified to exhibit varying width along its length. More particularly, as illustrated in FIG. 16A of the drawings, this latest form of the modified spring exhibits a tapered body, or an elongated band portion 122a.

Springs 122 can be constructed from various materials, such as metal, plastic, ceramic, composite and alloys, that is, intermetallic phases, intermetallic compounds, solid solution, metal-semi metal solutions including but not limited to Al/Cu, Al/Mn, Al/Si, Al/Mg, Al/Mg/Si, Al/Zn, Pb/Sn/Sb, Sn/Sb/Cu, Al/Sb, Zn/Sb, In/Sb, Sb/Pb, Au/Cu, Ti/Al/Sn, Nb/Zr, Cr/Fe, non-ferrous alloys, Cu/Mn/Ni, Al/Ni/Co, Ni/Cu/Zn, Ni/Cr, Ni/Cu/Mn, Cu/Zn, Ni/Cu/Sn. These springs comprise a novel modification of the prior art constant force springs to provide variable springs suitable for use in many diverse applications.

Figure 17:
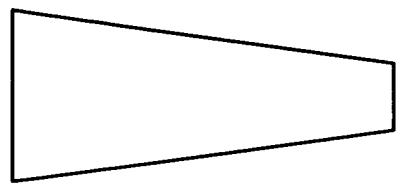
FIG. 17 is a generally illustrative view of the configuration of a retractable spring that would deliver a force that decreases by a factor of $w_1/w_2$ as a spring returned from its fully extended configuration to its fully coiled configuration.
Figure 18:
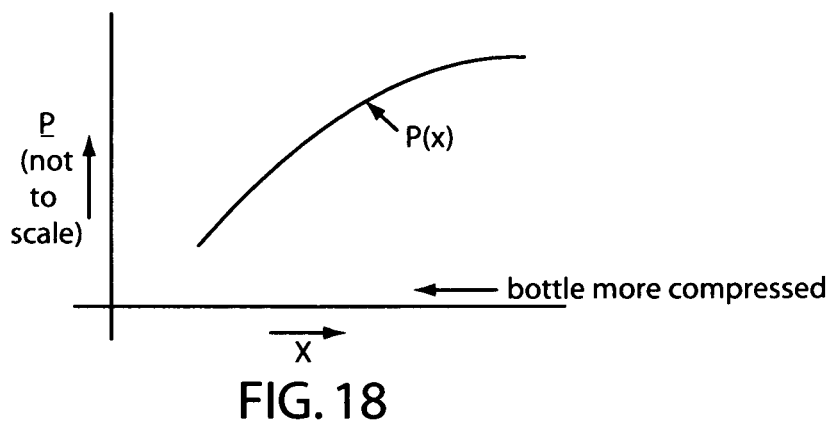
FIG. 18 is a generally graphical representation, plotting pressure versus the length of the reservoir container when a constant force spring is used to compress a bellows-like reservoir container.

With the foregoing in mind, if one wanted to produce a spring that delivered a force that increased by a factor of two as the spring returned from its fully extended conformation to its equilibrium, or fully coiled conformation, one would require that, as illustrated in FIG. 17 of the drawings, the width of the spring change by a factor of two along its length. In the example illustrated in FIG. 18, the force will decrease by a factor of $w_1/w_2$ as the spring changes from a fully extended configuration to a fully retracted configuration.

One form of the modified spring of this latest form of the invention can be described algebraically as follows: If x denotes the position of a point along a line that is parallel to the longitudinal axis of the spring and w(x) denotes the width of the spring at that point, then: $w(x) = (constant) x$. This describes the case wherein the width varies linearly with x as is shown in FIG. 17 of the drawings.

However, it is to be observed that the relationship between a position along the longitudinal axis of the spring and the width of the spring at that position need not be linear as shown in FIG. 17. Further, the width of the spring could be any arbitrary function of x. Thus: $w(x) = f(x)$ where (x) denotes an arbitrary function of x.

Figure 19:
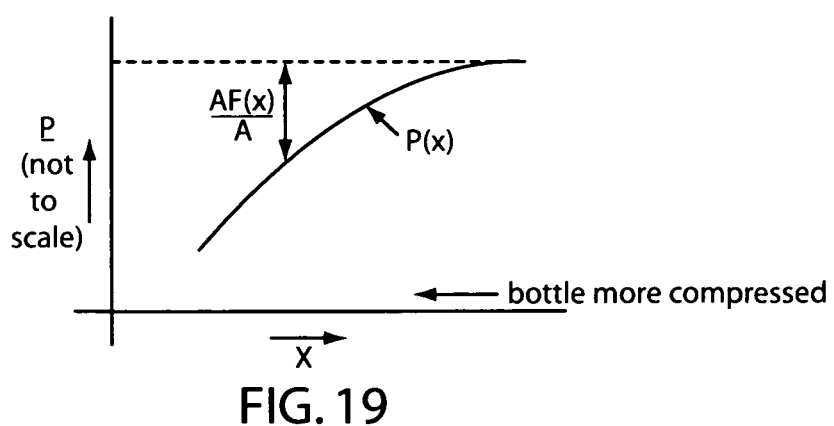
FIG. 19 is a generally graphical representation, similar to FIG. 13, plotting pressure versus the degree of compression for the reservoir container when the container is compressed by a constant force spring.

Using this concept, a spring can be designed that can be used to controllably compress a bellows type reservoir such as reservoir 56, which when compressed by the modified springs 120, exhibits a pressure vs. degree of compression curve of the character shown in FIG. 19. Stated another way, it is apparent that the concept can be employed to design a spring that generates a pressure that is independent of the degree of compression of the bellows-type reservoir.

By way of example, suppose that the pressure vs. degree of compression curve for a bellows-like container when compressed by a constant force spring is exemplified by the curve P(x) and the force of the constant force spring is "FCFS". Further assume that the drop in pressure as the container is compressed is due to the force "BF(x)", which is the force required to compress the container. Then the net force producing the pressure in the container can then be written: F(x)=FCFS−BF(x). Assume for simplicity that the area on which the force F acts is constant and is represented by "A". Then the pressure in the bottle is: P(x)=(FCFS−BF(x))/A. This equation describes, in functional form, the curve labeled P(x) in FIG. 18 and includes explicitly the contributions of the two forces generating the pressure within the reservoir 56 of the bellows-like container that is the force due to the spring and the force due to the bellows-like container.

The foregoing analysis allows one to design a spring, the force of which changes in such a way that the sum of all forces generating the pressure in the container is independent of the degree of the compression of the container, i.e., independent of the variable x. The force delivered by such a spring can be stated as: F(x)=FCFS+AF(x). Where "FCFS" is the force delivered by the original constant force spring and AF(x) is an additional force whose functional form is to be determined. Thus, the modified spring can be thought of as being composed of two parts, one part delivers the force of the original constant force spring (a force independent of x) and the other delivers a force that depends on the variable x.

For this system, the net force generating the pressure in the reservoir of the bellows-like collapsible container, such as container 46, is stated as: FS(x)=F.sub.ms(x)−BF(x)=FCFS+AF(x)−BF(x).

Assuming that: AF(x)=BF(x) for all x. Then the total force compressing the container is: FS(x)=FCFS+AF(x)−AF(x)=FCFS which force is independent of the degree of compression of the collapsible container, and wherein the pressure within the container is independent of the degree of compression of the container.

P.sub.ms(x)=(FCFS+AF(x)−AF(x))/A=FCFS/A. Where P.sub.ms(x) denotes the pressure in the fluid reservoir when the modified spring of the invention is used.

In designing the modified spring of this latest form of the invention, the information contained in the pressure vs. displacement curve when the container is compressed by a constant force spring can be used to determine how the cross-sectional mass, in this case the width of the spring, must vary as a function of x in order that the pressure in the container when compressed with the modified spring remains constant.

The force delivered by the spring being linearly dependent on the width of the spring if all other things remain constant, thus:

$$AF(x)=(\text{constant})w(x)$$

Substituting this into equation:

$$P(x)=(FCFS-BF(x))/A, \text{then:}$$

$$P(x)=(FCFS-AF(x))/A=(FCFS-\text{constant})w(x))A$$

However, it is to be observed that FCFS/A−P(x) is just the difference between the two curves shown in FIG. 19, FCFS/A being the horizontal line. Thus, the modification to the width, denoted w(x), of the original constant force spring is proportional to the difference between the two curves shown in FIG. 19. In other words, the shape of the change in the width of the spring as a function of x is similar to the difference between the two curves as a function of x. Furthermore, one can simply "read off" the shape of the curve w(x) from the pressure vs. displacement curve.

The broader utility of a variable force spring whose width defines the specific force may be that the spring design can be appropriately constructed to deliver a non-linear and highly variable force to meet a specific requirement. In this way, a spring that has a width that simply decreases as it is unrolled could be used. Alternatively, the spring could have an increasing width, followed by a width that decreases again during its distention. The spring force provided is therefore highly tunable to meet a variety of applications and requirements, simply by constructing a spring of specific width at the desired distension.

Once communication is established between the penetrating member and the reservoir 56 of the collapsible container in the manner previously described, the three circumferentially spaced, variable force springs 122 will continue to wind about their respective drums 122b and in so doing will cause the shuttle to move forwardly, causing the collapse of the collapsible container and the movement of the protuberance 60a into the position wherein it fills a substantial portion of the reservoir of the collapsible container. As the container collapses, the medicinal fluid contained within the reservoir will controllably flow into the internal passageway 32a of the penetrating member 32, through the rate control means of the invention and then to the administration set which is of the character previously described.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

The invention claimed is:

1. An apparatus for dispensing medicinal fluids to a patient comprising:
   (a) housing having first and second ends;
   (b) a first assembly connected to said first end of said housing, said first assembly comprising:
      (i) a front cover;
      (ii) a connecter member disposed within said front cover, said connecter member including an O-ring;
      (iii) a container positioning collar connected to said connecter member, said container positioning collar including an O-ring;
      (iv) a penetrating sub-assembly sealably connected to said connecter member, said penetrating sub assembly comprising a support member and a penetrating member connected to said support member, said penetrating member having a centrally disposed fluid passageway;
      (v) a rate control assembly connected to said penetrating sub-assembly for controlling the rate of fluid flow toward the patient, said rate control assembly including a rate control member having an inlet in communication with said fluid passageway of said penetrating member and having an outlet; and (vi) an administration set in communication with said outlet of said rate control assembly for delivering medicinal fluid to the patient;

(c) an internally threaded shuttle disposed within said housing;

(d) a collapsible container carried by said shuttle, said collapsible container comprising an integrally formed, hermetically sealed container having a neck portion sealably connected to said container positioning collar, an accordion sidewall connected to said neck portion, a pierceable top wall connected to said accordion sidewall, a pierceable membrane positioned over said pierceable top wall and a bottom wall connected to said side wall, said accordion sidewall, said pierceable top wall and said bottom wall being continuously formed and cooperating to define a reservoir for containing a medicinal fluid;

(e) an externally threaded operating member rotatably connected to said second end of said housing for rotation between first and second positions and being operably associated with said shuttle for moving said shuttle within said housing from a starting position to a first advanced position wherein said pierceable top wall of said collapsible container is disposed proximate said piercing member;

(f) stored energy means disposed within said housing and operably associated with said shuttle for moving said shuttle within said housing from said first advanced position to a second advanced position wherein said piercing member pierces said pierceable top wall of said collapsible container to open communication between said fluid passageway of said penetrating member and said reservoir of said collapsible container and then into a third advanced position wherein said side wall of said collapsible container is collapsed; and (g) a locking assembly for releasably locking said operating member in said first position, said locking assembly for releasably locking said operating member in said first position, said locking assembly comprising:
(i) a locking member having a central portion having a plurality of arcuate shaped grooves; and
(ii) a pusher member connected to said locking member, said pusher member being movable between a first extended position and a second retracted position, said pusher member having a plurality of outwardly extending members receivable within said plurality of arcuate shaped grooves.

2. The apparatus as defined in claim 1 in which said bottom wall of said collapsible container includes an inwardly extending protuberance.

3. The apparatus as defined in claim 1 in which said rate control member has a micro-channel etched therein, said micro-channel having a width of between about 0.025 in. and about 0.127 in. and a depth of between about 0.025 in. and about 0.127 in.

4. The apparatus as defined in claim 1 in which said container positioning collar has a flange portion in engagement with said accordion wall of said container.

5. The apparatus as defined in claim 1 further including a retainer collar affixed to said neck portion of said collapsible container for holding said pierceable membrane in position.

6. The apparatus as defined in claim 1 in which said hollow housing is provided with a plurality of circumferentially spaced apart, longitudinally extending guide grooves and in which said shuttle includes a protuberance slidably receivable within said circumferentially spaced apart guide grooves of said hollow housing.

7. An apparatus for dispensing fluids to a patient comprising:

(a) housing having first and second ends;

(b) a first assembly connected to said first end of said housing, said first assembly comprising:
(i) body portion;
(ii) a penetrating sub-assembly connected to said body portion, said penetrating sub-assembly comprising a support member and a penetrating member connected to said support member, said penetrating member having a fluid passageway; and
(iii) a rate control assembly connected to said penetrating sub-assembly, said rate control assembly including a rate control member having a micro-channel formed therein, said micro-channel having an inlet in communication with said fluid passageway of said penetrating member and an outlet;

(c) a shuttle disposed within said housing;

(d) a collapsible container carried by said shuttle, said collapsible container comprising an integrally formed, hermetically sealed container having an accordion sidewall, a pierceable top wall connected to said accordion sidewall and a bottom wall connected to said sidewall, said accordion sidewall, said pierceable top wall and said bottom wall being continuously formed and cooperating to define a reservoir for containing a medicinal fluid;

(e) a rotatable operating member connected to said second end of said housing and threadably connected to said shuttle for rotation relative thereto for advancing said shuttle within said housing from a starting position to a first advanced position wherein said pierceable top wall of said collapsible container is disposed proximate said piercing member;

(f) stored energy means disposed within said housing and operably associated with said shuttle for moving said shuttle within said housing from said first advanced position to a second advanced position wherein said piercing member completely pierces said pierceable top wall of said collapsible container to open communication between said fluid passageway of said penetrating member of said reservoir of said collapsible container;

(g) an administration set connected to said housing, said administration set being in communication with said outlet of said micro-channel; and (h) a locking assembly for releasably locking said operating member in said starting position, said locking assembly comprising:
(i) a generally planar locking member including a generally circular shaped central portion having a central aperture having a plurality of generally arcuate shaped grooves; and
(ii) a pusher member connected to said locking member, said pusher member being movable between a first extended position and a second retracted position, said pusher member having a plurality of outwardly extending members receivable within said plurality of generally arcuate shaped grooves.

8. An apparatus for dispensing fluids to a patient comprising:

(a) housing having first and second ends;

(b) a first assembly connected to said first end of said housing, said first assembly comprising:
(i) body portion;
(ii) a penetrating sub-assembly connected to said body portion, said penetrating sub-assembly comprising a support member and a penetrating member connected to said support member, said penetrating member having a fluid passageway; and
(iii) a rate control assembly connected to said penetrating sub-assembly, said rate control assembly including a rate control member having a micro-channel formed therein in communication with said fluid passageway of said penetrating member;
(c) a second assembly connected to said housing for movement relative thereto between a first position and a second position, said second assembly comprising:
(i) a shuttle;
(ii) a collapsible container carried by said shuttle; and
(iii) stored energy means operably associated with said shuttle for moving said shuttle within said housing;
(d) a third assembly connected to said housing proximate said second end thereof, said third assembly comprising a rotatable operating member connected to said shuttle for rotational movement relative thereto between a first position and a second position to act upon said shuttle to move said shuttle of said second assembly within said housing from a first position to a second position; and
(e) a locking assembly for releasably locking said operating member in said first position, said locking assembly comprising:
(i) a generally planar locking member having a generally circular central portion having a central aperture having a plurality of generally arcuate shaped grooves and a plurality of circumferentially spaced apart, radially outwardly extending arms; and
(ii) a pusher member connected to said locking member, said pusher member being movable between a first extended position and a second retracted position, said pusher member having a plurality of outwardly extending members receivable within said plurality of arcuate shaped grooves.

* * * * *